US005719061A

United States Patent [19]

Rose-Pehrsson et al.

[11] Patent Number: 5,719,061

[45] Date of Patent: Feb. 17, 1998

[54] FLUORESCENT DETECTION OF HYDRAZINE, MONOMETHYLHYDRAZINE, AND 1,1-DIMETHYLHYDRAZINE BY DERIVATIZATION WITH AROMATIC DICARBOXALDEHYDES

[75] Inventors: Susan Rose-Pehrsson, Alexandria, Va.; Gregory E. Collins, Waldorf, Md.

[73] Assignee: The United States of America as represented by the Secretary of the Navy, Washington, D.C.

[21] Appl. No.: 326,518

[22] Filed: Oct. 20, 1994

[51] Int. Cl.[6] .......... G01N 33/22; G01N 33/00

[52] U.S. Cl. .......... 436/171; 436/106; 436/166; 436/169

[58] Field of Search .......... 436/106, 112, 436/169, 166

[56] References Cited

U.S. PATENT DOCUMENTS

| | | | |
|---|---|---|---|
| 4,780,282 | 10/1988 | Holtzclaw et al. | 422/56 |
| 4,900,681 | 2/1990 | Taffe et al. | 436/106 |

OTHER PUBLICATIONS

C.S. Marvel et al. *J. Am. Chem. Soc.* 1950, 72, 4819–4820.
R.F. Smith et al. *J. Org. Chem*, 1962, 27, 879–882.
A. Hirsch et al *J. Heterocyc. Chem.* 1965, 2, 206.
A. Mallouli et al. *Synthesis* 1980, 689.
F. DeSio et al. *Heterocycles* 1983, 20, 1279–1284.
A. Rios et al. *Anal. Chim. Acta* 1980, 187, 139–145.
G.E. Collins et al. *Anal. Chim. Acta*, 1993, 284, 207–215.
Weeks et al. Anal. Chem., 48(1), 1976, 159–161.
Danielson et al., Talauta, 29(5), 1982, 401–4.
Lai et al. (Abstract, AN 1993:517765, Hcaplus).
Kwakman et al. (Abstract, AN 1990: 564708 Hcaplus.
J.R. Wyatt et al., *Coulometric Method for the Detection of Low–Level Concentrations of Hydrazine and Monomethylhydrazine*, Am. Ind. Hyg. Assoc. J. 54(6):285–292 (1993).
Collins et al., *Sensitive Fluorescent Detection of Hydrazine via Derivatization with 2,3–naphtalene dicarboxaldehyde*, Analytica Chimica Acta, vol. 284, pp. 207–215 (Dec. 1993).
Collins et al., *The Fluorescent Detection of Hydrazine, Monomethyl–hydrazine, and 1,1–dimethylhydrazine by Derivatization with Aromatic Dicarboxaldehydes*, Optical Sensing for Env. Monitoring, pp. 732–739 (1994).
Pehrsson, Current State–of–the–Art in Hydrazine Sensing, Proceedings (Sensors Expo) pp. 37–41 (1994).
Collins et al., The Detection of PPB Levels of Hydrazine Using Fluorescence and Chemiluminescence Techniques, pp. 1–10, Proceedings (Sensors Expo) (1994).

(List continued on next page.)

*Primary Examiner*—Arlen Soderquist
*Attorney, Agent, or Firm*—Thomas E. McDonnell; Barry Edelberg

[57] ABSTRACT

A method and apparatus for the detection of hydrazine, monomethylhydrazine, 1,1-dimethylhydrazine in air (or other gas medium) or in an aqueous solution. The detection is accomplished by introducing a stream of air, or other gas medium, or aqueous solution suspected of containing hydrazine, monomethylhydrazine, 1,1-dimethylhydrazine or mixtures thereof into a pH controlled reagent solution containing an aromatic dicarboxaldehyde to react with the hydrazine, monomethylhydrazine, 1,1-dimethylhydrazine or mixtures thereof, respectively, and by exposing the reacted reagent solution to an excitation wavelength range and monitoring an emission from the exposed reagent solution at an emission wavelength range to detect the presence of a hydrazine derivative, monomethylhydrazine derivative, 1,1-dimethylhydrazine derivative, or mixtures thereof (i.e. a derivative formed by the reaction between hydrazine, monomethylhydrazine, 1,1-dimethylhydrazine and the aromatic dicarboxaldehyde) indicating the presence of hydrazine, monomethylhydrazine, 1,1-dimethylhydrazine or mixtures thereof within the stream of air or other gas medium or aqueous solution.

31 Claims, 17 Drawing Sheets

OPA NDA ADA

Hz MMH UDMH

OTHER PUBLICATIONS

Collins et al., Fluorescent Detection of Hydrazine, Monomethylhydrzine, 1,1–Dimethylhydrazine by Derivatization with Aromatic Dicarboxaldehydes, Analyst, vol. 119, pp. 1907–1913 (Aug. 1994).

Collins et al., Fluorescent Detection of Hydrazine, Monomethylhydrazine, and 1,1–Dimethylhydrzine by Derivatization with Dicarboxaldehydes, CPIA Publication 600, pp. 11–20 (1993).

Letter from Lori Pickett of CPIA dated 04 Oct. 1994.

| REAGENT | $\lambda_{ex}$ (nm) | $\lambda_{em}$ (nm) |
|---|---|---|
| OPA | 318 | 376 |
| NDA | 403 | 500 |
| ADA | 476 | 549 |

FIG. 10

| REAGENT (M/L) | | | HYDRAZINE | | | |
|---|---|---|---|---|---|---|
| (OPA) | (NDA) | (ADA) | (HZ) | (MMH) | (UDMH) | FIGURE |
| $2.3X10^{-3}$ | ---------- | ---------- | $1.4X10^{-5}$ | ---------- | ---------- | 4 |
| ---------- | $2.4X10^{-4}$ | ---------- | $7.4X10^{-7}$ | ---------- | ---------- | 4,8 |
| ---------- | $2.4X10^{-6}$ | ---------- | ---------- | $5.2x10^{-7}$ | ---------- | 8 |
| ---------- | $2.4x10^{-6}$ | ---------- | ---------- | ---------- | $3.1x10^{-4}$ | 8 |
| ---------- | ---------- | $1.9x10^{-6}$ | $7.4x10^{-8}$ | ---------- | ---------- | 4 |

FIG. 11

| REAGENT (M/L) | | | | |
|---|---|---|---|---|
| (OPA) | (NDA) | (ADA) | (HZ) | pH |
| $4.5 \times 10^{-6}$ | ---------- | ---------- | $1.4\text{-}29 \times 10^{-5}$ | 2.5 |
| ---------- | $2.4 \times 10^{-8}$ | ---------- | $1.5\text{-}28 \times 10^{-4}$ | 2.5 |
| ---------- | ---------- | $1.9 \times 10^{-7}$ | $1.2\text{-}14 \times 10^{-6}$ | 6 |
| $4.8\text{-}130 \times 10^{-5}$ | ---------- | ---------- | $4.3 \times 10^{-6}$ | 2.5 |
| ---------- | $4.8\text{-}590 \times 10^{-5}$ | ---------- | $7.4 \times 10^{-7}$ | 2.5 |
| ---------- | ---------- | $3.9\text{-}3.7 \times 10^{-7}$ | $7.5 \times 10^{-8}$ | 13.5 |

FIG. 12

FLUORESCENT DETECTION OF HYDRAZINE, MONOMETHYLHYDRAZINE, AND 1,1-DIMETHYLHYDRAZINE BY DERIVATIZATION WITH AROMATIC DICARBOXALDEHYDES

BACKGROUND OF THE INVENTION

1. Field of the Invention

The present invention relates to a method for the detection of hydrazine (Hz), monomethylhydrazine (MMH) and 1,1-dimethylhydrazine (UDMH). More particularly the present invention relates to the detection of hydrazine, on a real time basis, down to a concentration of about 1 to about 10 parts per billion (ppb) in air (or other gaseous medium) or down to 50 ng/L in aqueous solution.

2. Description of the Related Art

Interest in the development of new methods for the detection of hydrazine, $N_2H_4$, has paralleled its use in increasing numbers of applications as both a primary industrial chemical as well as a hypergolic fuel propellent. Hydrazine is an important building block essential to the synthesis of a number of polymers, pesticides, pharmaceuticals, and chemotherapeutic tools. Because of the strong reducing capability of hydrazine in basic solution and the fact that its oxidation products are nitrogen and water, electric utilities employ hydrazine as an effective chemical for preventing the corrosion of boilers by dissolved oxygen and metal oxides. The Department of Defense and NASA have taken advantage of the hypergolic properties of hydrazine for a number of years as propellents for the space shuffle, satellites and aircraft auxiliary-power units.

Recent medical studies have indicated that there are various toxicological problems associated with hydrazine exposure. Hydrazine is suspected to result in a number of adverse effects in man, including: damage to the liver, kidneys, and other internal organs; production of various blood abnormalities; irreversible damage to the nervous system; an alteration in the behavior of those exposed; and numerous teratogenic and mutagenic effects. Because of the health hazards associated with hydrazine, the American Conference of Governmental Industrial Hygienist (ACGIH) has recommended that the threshold limit value (TLV) for hydrazine be lowered from 100 ppb to 10 ppb in air. The TLV is a time-weighted average concentration of permissible exposure within a normal eight hour workday. Specifications for a hydrazine sensor mandate, in view of the lower TLV, that it have a detection limit of 1 ppb for hydrazine and a response time of (the time necessary for a 90% change in the total response) about 2–15 minutes or less. This type of sensitive and selective, on-line monitor for hydrazine, operating at the new TLV level, would likely be applicable to a number of industrial situations.

Several different methods developed for the detection of low levels of hydrazine do not meet the real time and/or the detection limit requirements of a suitable monitoring system. The first passive dosimeter system for hydrazine detection is referred to as a titrate sampler and is reliant upon a citric acid coating to trap and stabilize the hydrazines for subsequent analysis by wet chemical techniques. The second passive dosimeter system for hydrazine detection is referred to as a colorimetric technique which incorporates both 2,4-dinitrobenzaldehyde and vanillin (3-methoxy-4-hydroxybenzaldehyde) as separate detectors onto a single badge, allowing for the simultaneous quantitation of both hydrazine and (UDMH). While these badges are effective passive sampling devices, they do not provide active and continuous real-time monitoring of hydrazine concentration. The colorimetric reactions that take place between hydrazine and a number of different benzaldehydes (i.e. para-dimethylbenzaldehyde, salicaldehyde) have also been utilized in various flow-injection analysis schemes. The detection limits for these absorbance techniques are ultimately limited by the nature of the absorbance measurement to be approximately 5–10 μg/l of hydrazine in solution. The detection limit of 5–10 μg/l of hydrazine in solution makes this approach inadequate for detecting hydrazines down to 10 ppb in air or other gas medium. For potentiometry and coulometry techniques for the detection of hydrazine, their sensitivity, detector life-time limitations, and/or inappropriateness as real time continuous monitors of hydrazine concentration have been the limiting problems for these techniques. The expense and operator expertise associated with some mass spectrometric methods used for the detection of hydrazine are the primary disadvantages associated with these techniques.

Thus, there is a need for a method and apparatus for the detection of hydrazine (Hz), monomethylhydrazine (MMH) and 1,1 dimethylhydrazine (UDMH) that is done on a real-time continuous basis. There is a further need for a method and apparatus for the detection of hydrazine (Hz), monomethylhydrazine (MMH) and 1,1 dimethylhydrazine (UDMH) wherein the detection limit of 1 ppb for hydrazine (in air or other gaseous medium) is reached. There is an even further need for a method and apparatus for the detection of hydrazine (Hz), monomethylhydrazine (MMH) and 1,1 dimethylhydrazine (UDMH) wherein little or no expertise or training is needed to utilize the hydrazine detection method. There is yet a further need for a method and apparatus for the detection of hydrazine (Hz), monomethylhydrazine (MMH) and 1,1 dimethylhydrazine (UDMH) wherein the detection can be accomplished within about 2 to about 15 minutes. There is yet an even further need for a method and apparatus for the detection of hydrazine (Hz), monomethylhydrazine (MMH) and 1,1 dimethylhydrazine (UDMH) wherein the detection method utilizes a fluorescence detection scheme that is simpler and easier to practice than complicated methods such as mass spectrometry. In addition, there is a need for a method and apparatus for the detection of hydrazine (Hz), monomethylhydrazine (MMH) and 1,1 dimethylhydrazine (UDMH) wherein the method is selective to the hydrazines (i.e. Hz, MMH and UDMH) in air (or other gaseous medium) or in aqueous solution.

SUMMARY OF THE INVENTION

Thus it is an object of the present invention to develop a method and apparatus for the detection of hydrazine (Hz), monomethylhydrazine (MMH) and 1,1 dimethylhydrazine (UDMH) that is done on a real-time continuous basis.

It is a further object of the present invention to develop a method and apparatus for the detection of hydrazine (Hz), monomethylhydrazine (MMH) and 1,1 dimethylhydrazine (UDMH) wherein the detection limit of 1 ppb for hydrazine (in air or other gas medium) is reached.

It is an even further object of the present invention to develop a method and apparatus for the detection of hydrazine (Hz), monomethylhydrazine (MMH) and 1,1 dimethylhydrazine (UDMH) wherein little or no expertise or training is needed to utilize the hydrazine detection method.

It is yet a further object of the present invention to develop a method and apparatus for the detection of hydrazine (Hz), monomethylhydrazine (MMH) and 1,1 dimethylhydrazine (UDMH) wherein the detection can be accomplished within about 2 to about 15 minutes.

It is yet an even further object of the present invention to develop a method and apparatus for the detection of hydrazine (Hz), monomethylhydrazine (MMH) and 1,1 dimethylhydrazine (UDMH) wherein the detection method utilizes a fluorescence detection scheme that is simpler and easier to practice than complicated methods such as mass spectrometry.

It is another object of the present invention to develop a method and apparatus for the detection of hydrazine (Hz), monomethylhydrazine (MMH) and 1,1 dimethylhydrazine (UDMH) wherein the method is selective to the hydrazines (i.e. Hz, MMH and UDMH) in air (or other gaseous medium) or in aqueous solution.

These and other objects are accomplished by introducing a stream of air or other gas medium or aqueous solution suspected of containing hydrazine, monomethylhydrazine and/or 1,1-dimethylhydrazine into a pH controlled reagent solution containing an aromatic dicarboxaldehyde to react the aromatic dicarboxaldehyde with the hydrazine, by exposing the reacted reagent solution to an excitation wavelength range and recording an emission from the exposed reagent solution at an emission wavelength range to detect the presence of a hydrazine derivative, a monomethylhydrazine derivative, and/or a 1,1-dimethylhydrazine derivative (i.e. derivatives formed by the reaction between hydrazine, monomethylhydrazine and/or 1,1-dimethylhydrazine and an aromatic dicarboxaldehyde, respectively) indicating the presence of hydrazine, monomethylhydrazine, and/or 1,1-dimethylhydrazine within the stream of air or other gas medium or aqueous solution.

Alternatively, a solid support material with one or more immobilized aromatic dicarboxaldehydes upon the solid support material could be used for the fluorescent detection of Hz; MMH and/or UDMH in air or other gaseous medium or in aqueous solution. After exposure of the aforementioned solid support material to either of Hz, MMH and/or UDMH, the solid support would be tested for a fluorescence signal at the appropriate emission wavelength range in response to exposure to the appropriate excitation wavelength range.

DETAILED DESCRIPTION OF THE DRAWINGS

A more complete appreciation of the present invention and several of the accompanying advantages thereof will be readily obtained by reference to the following detailed description when considered in conjunction with the accompanying drawings.

FIG. 1 shows the molecular structures of the derivatizing agents ortho-phthalaldehyde (OPA), napthalene 2,3-dicarboxaldehyde (NDA) and anthracene 2,3-dicarboxaldehyde (ADA) and the hydrazines (Hz, MMH, and UDMH) under study.

FIG. 2 is the emission spectra ($\lambda_{em}$) obtained for OPA, NDA, and ADA following the addition of 0, 4.3, 25, and 105 μg/L of hydrazine. In addition, the emission spectrum from the addition of 440 μg/L of hydrazine to the OPA reagent is also shown. In other words, FIG. 2 contains a set of emission spectra collected for napthalene 2,3-dicarboxaldehyde (NDA) ($\lambda_{ex}$=403 nm; $\lambda_{em}$=500 nm), for ortho-phthalaldehyde (OPA) ($\lambda_{ex}$=318 nm; $\lambda_{em}$=376 nm) and for anthracene 2,3-dicarboxaldehyde (ADA) ($\lambda_{ex}$=476 nm; $\lambda_{em}$=549 nm) fluorescent derivatives formed following the sequential addition of 0, 4.3, 25, and 105 μg/L of hydrazine to the NDA, OPA and ADA reagent solutions, respectively. Moreover, the emission spectrum for the OPA reagent solution following the addition of 440 μg/L, of hydrazine to the OPA reagent solution is also plotted.

Figure 5:
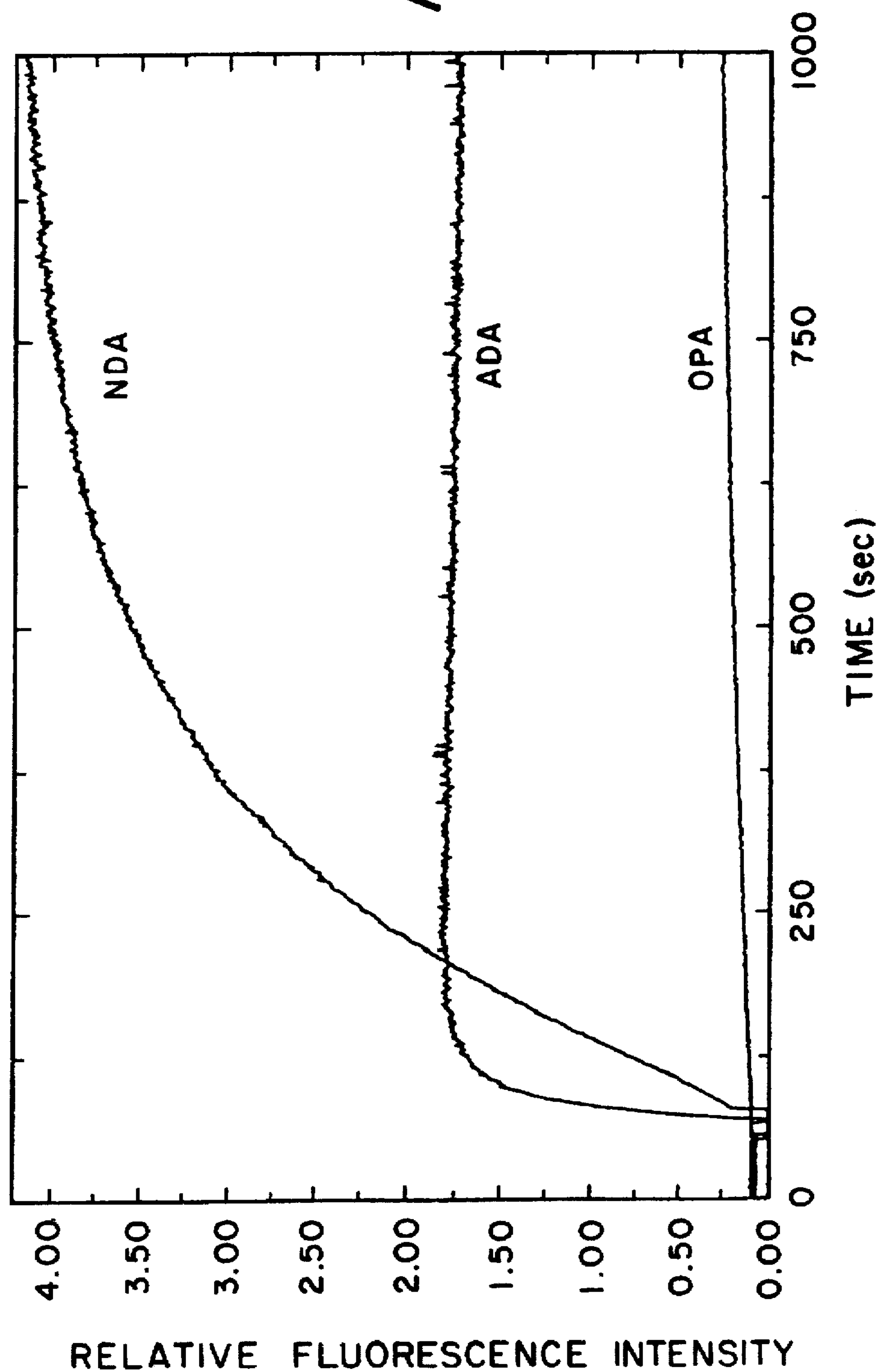

FIG. 5 is a plot of relative fluorescence intensity versus time resulting from the formation of the fluorescent OPA, fluorescent NDA, and fluorescent ADA derivatives of hydrazine following the introduction of 45 μg/L of hydrazine into the OPA, NDA and ADA reagent solutions, respectively. There is a 100 second offset prior to introduction of the hydrazine in order to establish the baseline intensity. The formation rates of the fluorescent OPA, fluorescent NDA and fluorescent ADA are determined from this plot.

Figure 6:
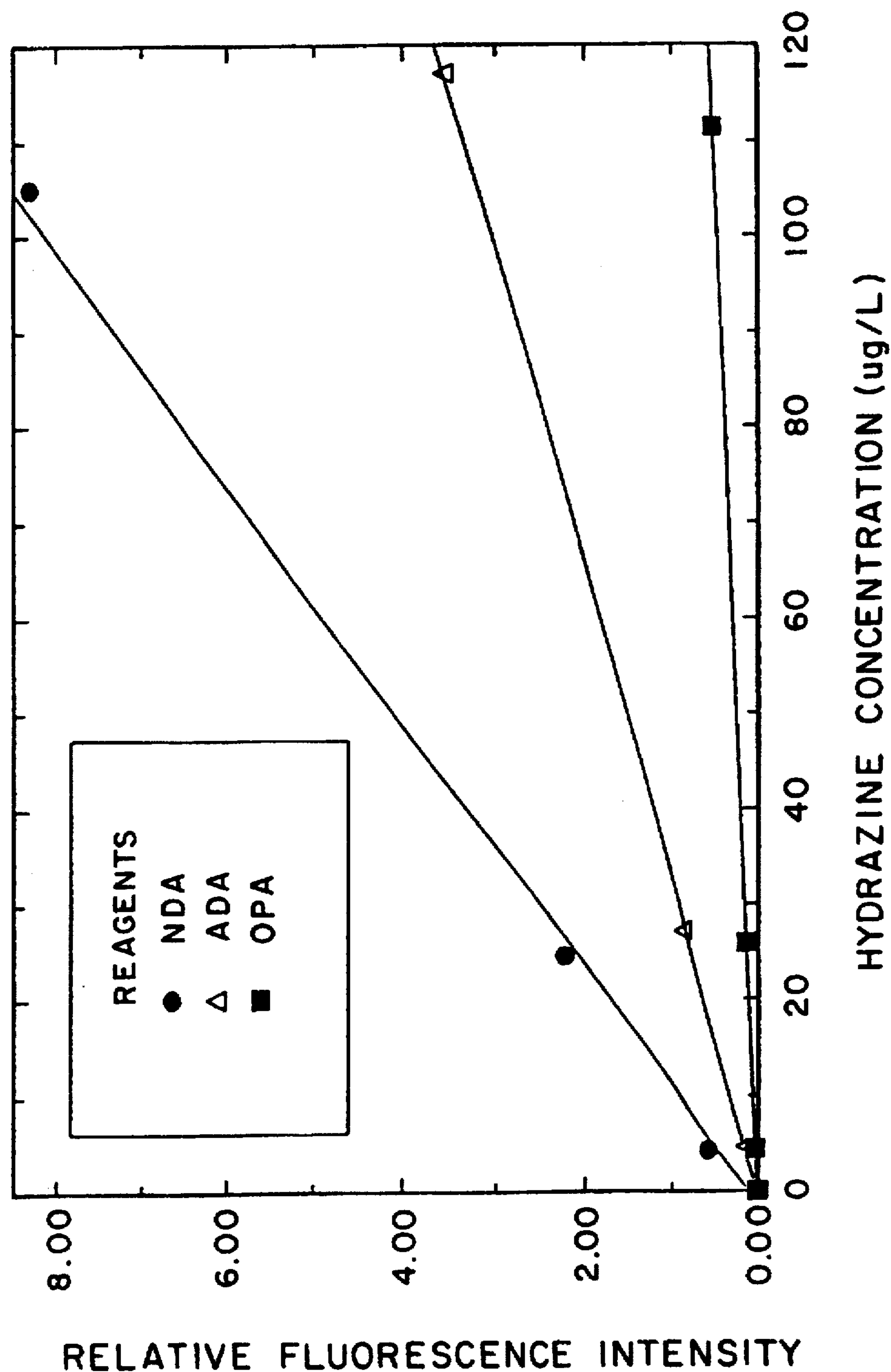

FIG. 6 is a plot of the relative fluorescence intensity versus hydrazine concentration for the emissions obtained for the fluorescent hydrazine derivatives formed with OPA, NDA, and ADA, respectively, at varying concentrations of hydrazine. The concentration dependence of the fluorescence intensities for the hydrazine derivatives is apparent.

Figure 7:
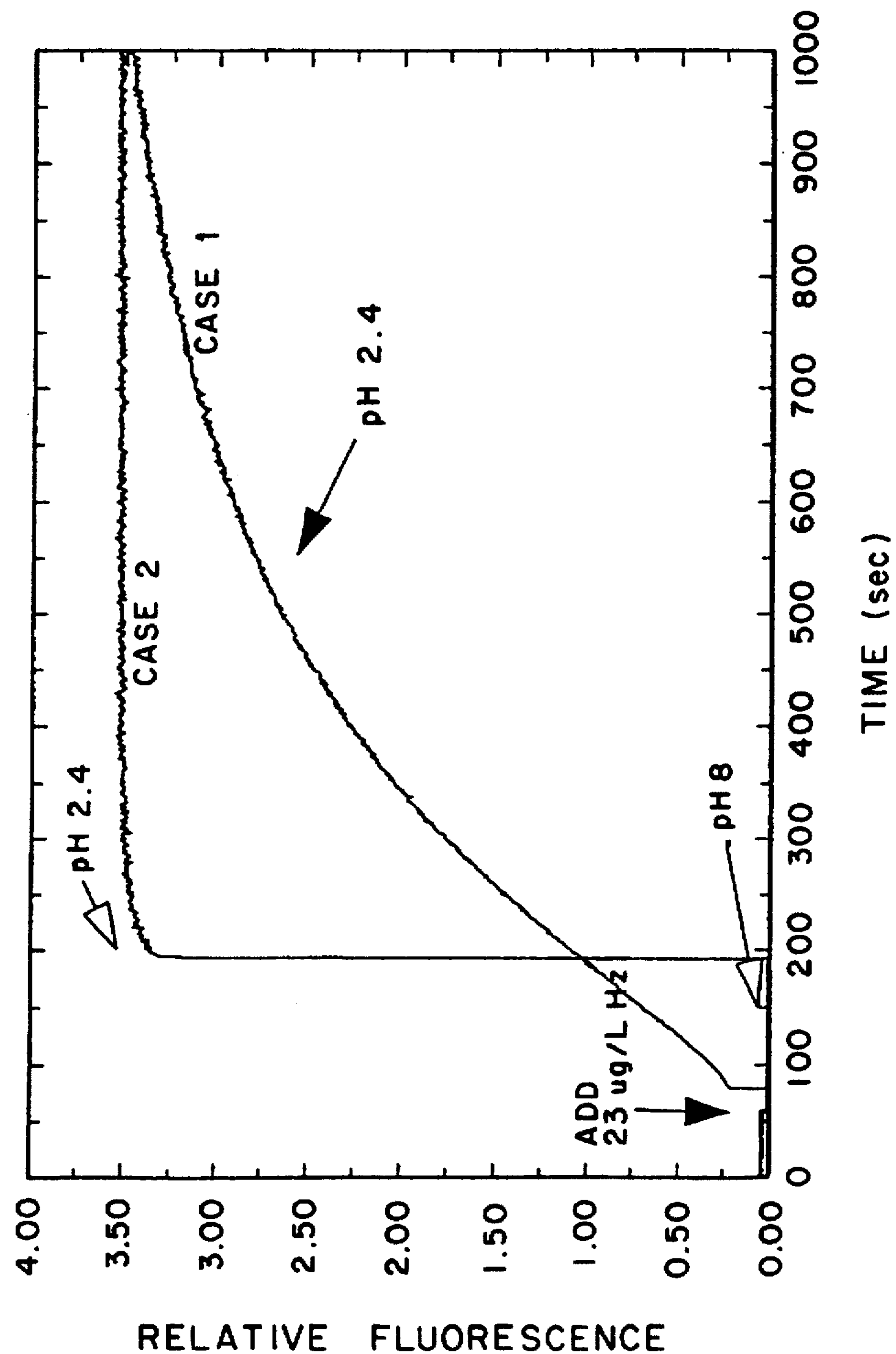

FIG. 7 is a comparison of the time response for the formation of the fluorescent NDA/Hz derivative following the addition of 23 μg/L of Hz to solutions under two different pH conditions.

Figure 8:
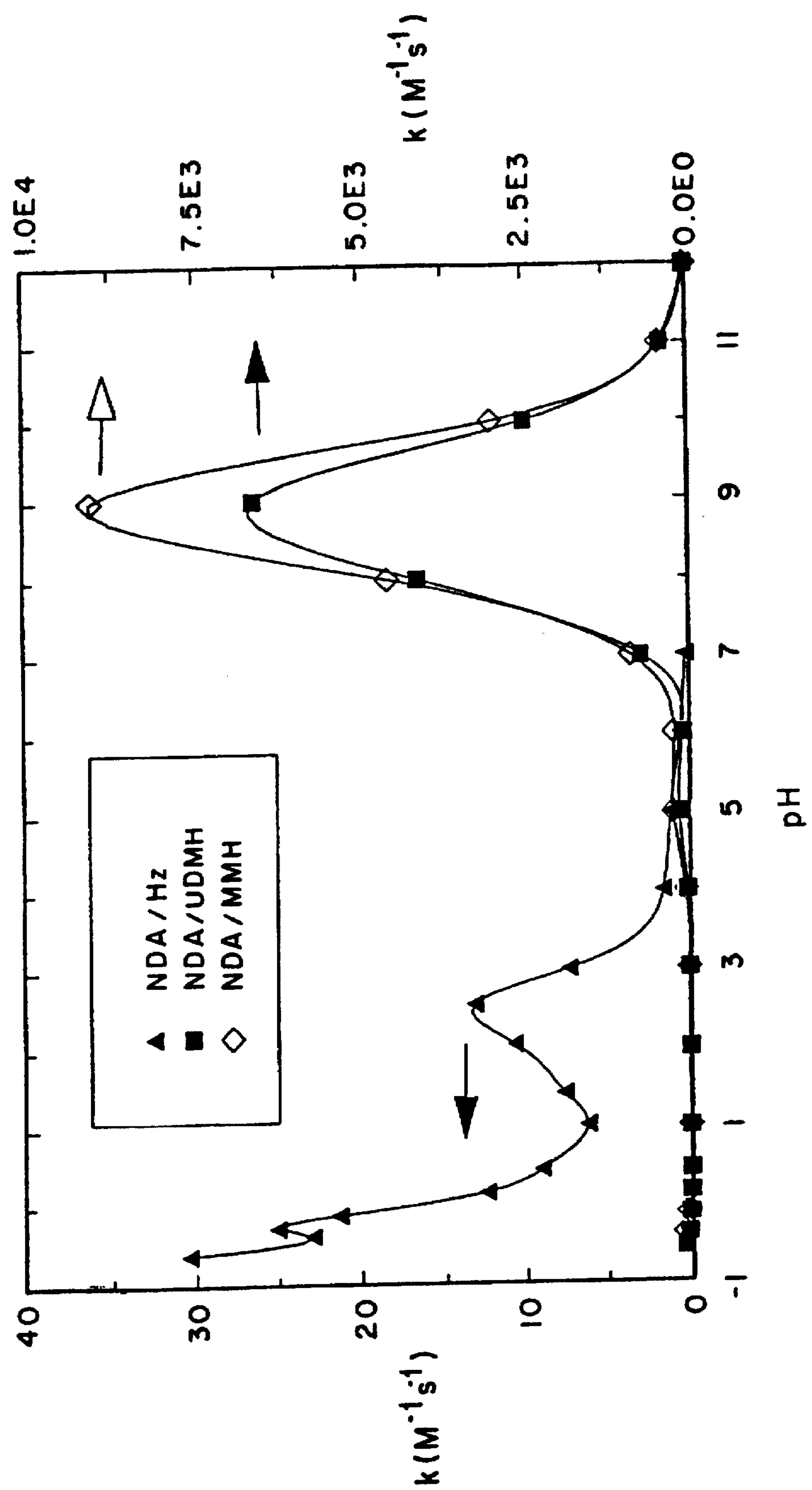

FIG. 8 shows the pH dependence of the formation rates for the fluorescent derivatives of NDA with Hz, NDA with MMH and NDA with UDMH, respectively.

Figure 9:
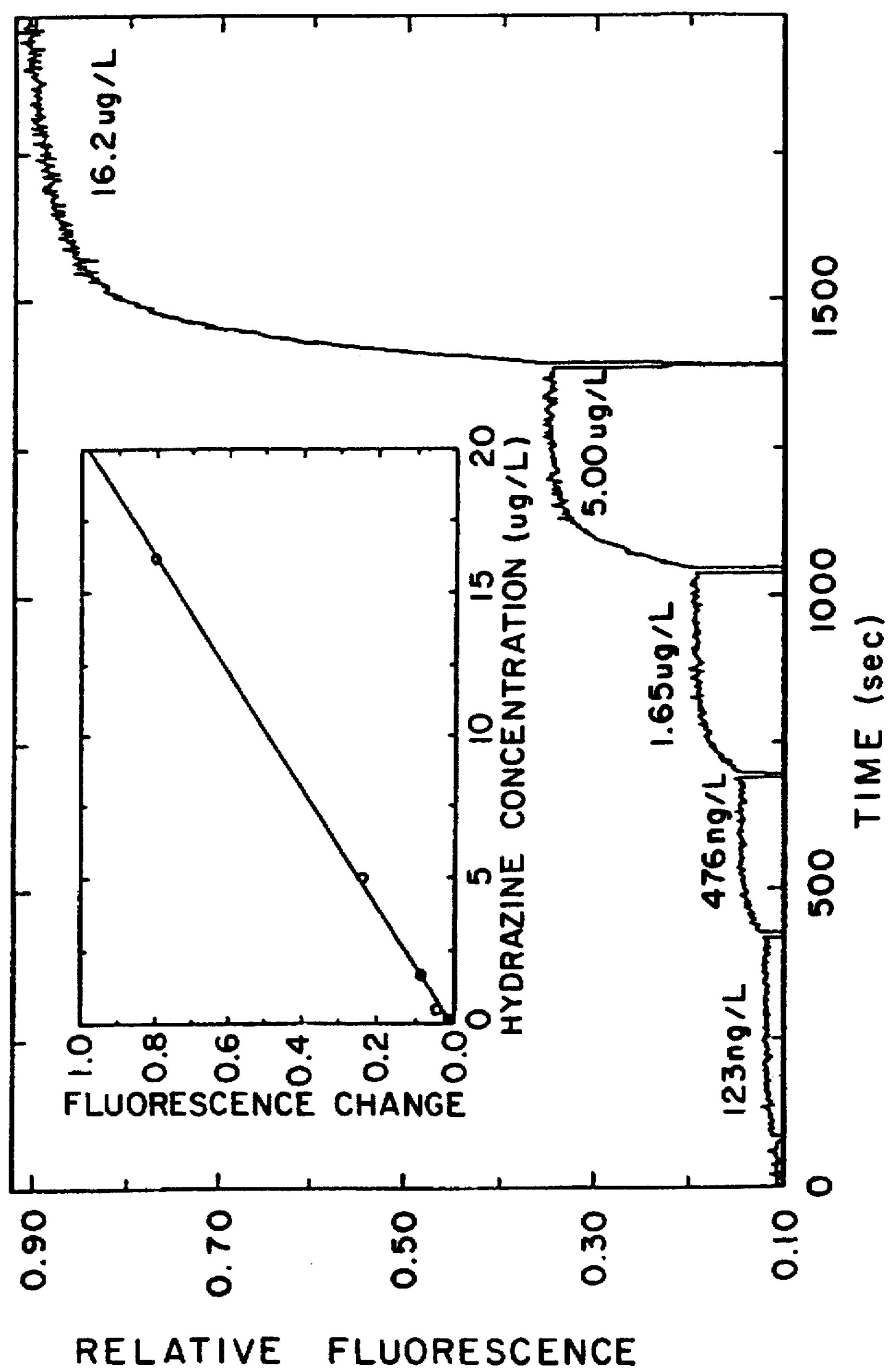

FIG. 9 depicts the fluorescence response of the NDA reagent following repeated additions of hydrazine. FIG. 9 shows the fluorescence response as measured by the emission ($\lambda_{ex}$=403 nm; $\lambda_{em}$=500 nm) following the sequential addition of hydrazine at concentrations from 123 ng/L, 476 ng/L, 1650 ng/L, 5000 ng/L, and 16,200 ng/L. Note that the response time necessary to give 90% of a full-scale response is less than 2 minutes. With each subsequent addition of hydrazine, the fluorescence at 500 nm ($\lambda_{em}$=500 nm) increases proportionally. The inset is a plot of these fluorescence changes as a function of the concentration of hydrazine added. In other words, the inset figure is a plot of the fluorescence change seen as a function of the concentration of hydrazine added. The NDA reagent gives excellent linear response to hydrazine at the levels plotted, as well at significantly higher hydrazine concentrations. A linear concentration dependence is observed over a dynamic range from 50 ng/L to 500,000 ng/L of hydrazine (correlation coefficient of r>0.999), with a signal-to-noise ratio of 3:1 for 50 ng/L of hydrazine. The response of the ADA reagent is similar (not shown) with the exception that its response time is significantly more rapid (less than 30 seconds) and its detection limit is higher at 200 ng/L.

FIG. 10 is a table of the excitation ($\lambda_{ex}$) and emission ($\lambda_{em}$) wavelengths used in the detection of the different hydrazine derivatives.

Figure 4:
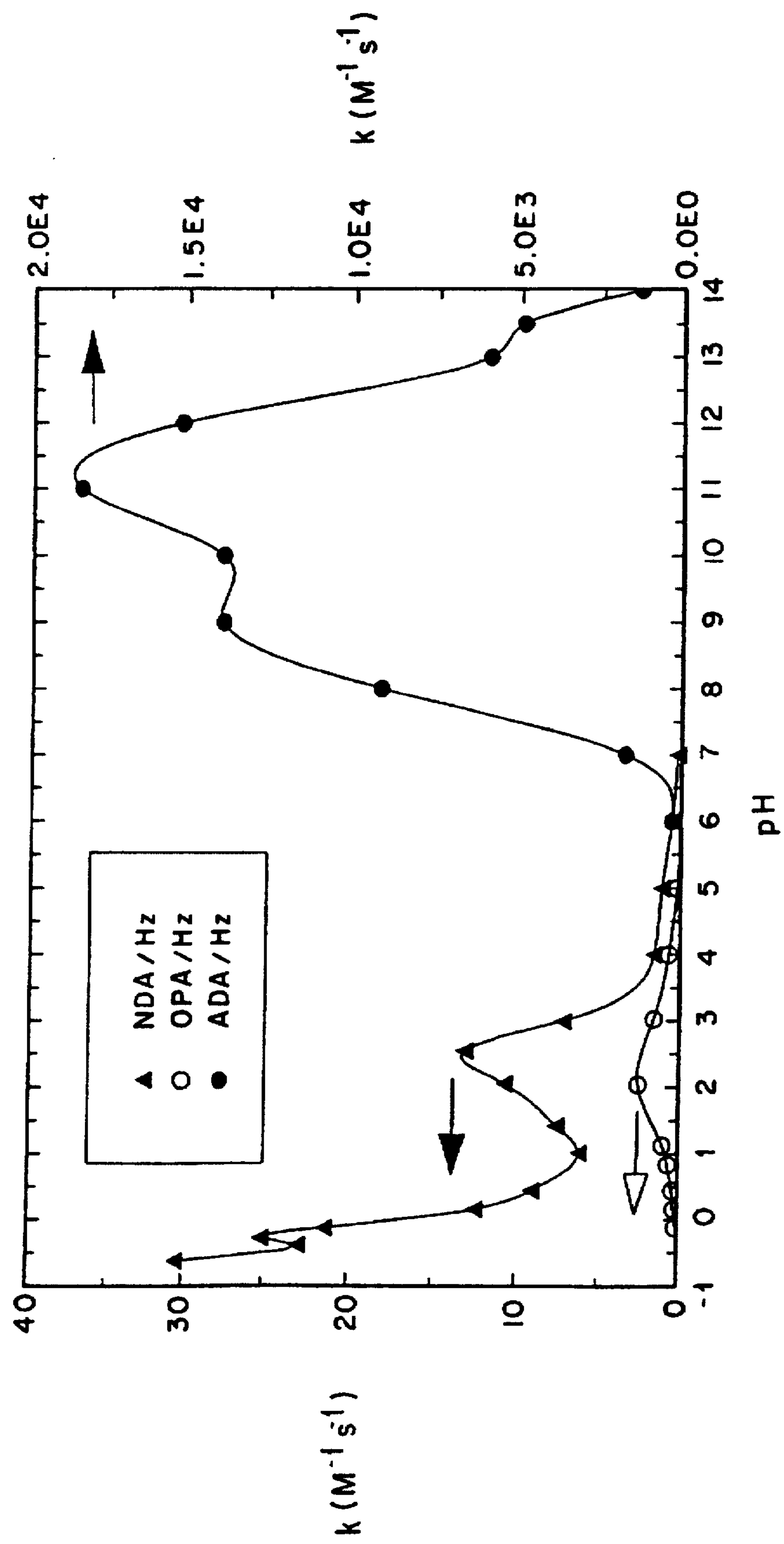
FIG. 4 is a plot of the formation rate constants of the fluorescent OPA, fluorescent NDA, and fluorescent ADA derivatives of hydrazine as a function of the pH.

FIG. 11 is a table which gives the reagent and analyte concentrations used for the pH profiles shown in FIGS. 4 and 8.

FIG. 12 is a table which gives the reagent and analyte concentrations used for studying the kinetic dependence of the hydrazines (Hz, MMH and UDMH) and the dicarboxaldehydes (OPA, NDA and ADA).

Figure 13:
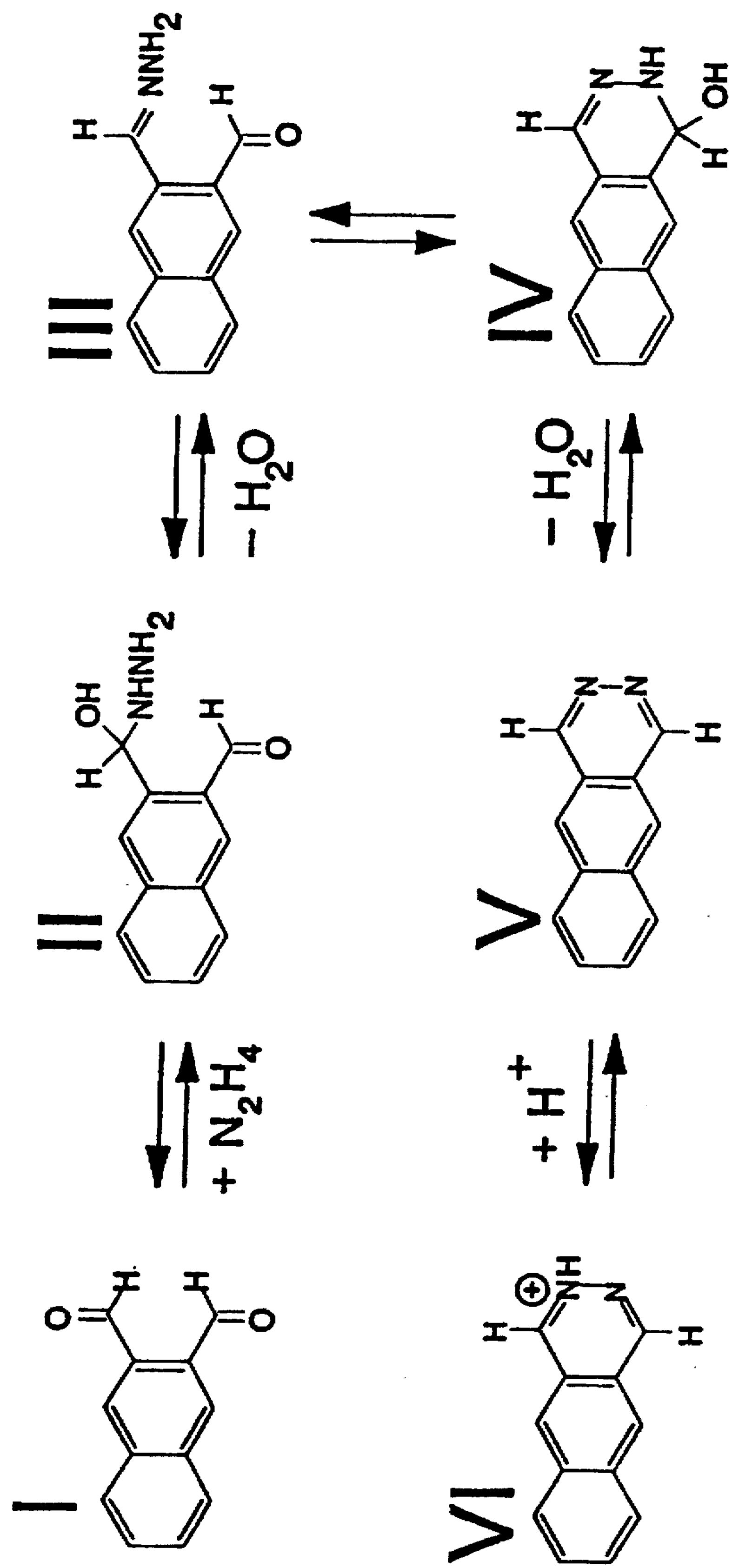

FIG. 13 shows the derivatization scheme for the reaction between hydrazine (Hz) and NDA. Similar mechanisms are projected in the reactions of hydrazine with either OPA or ADA.

Figure 14:
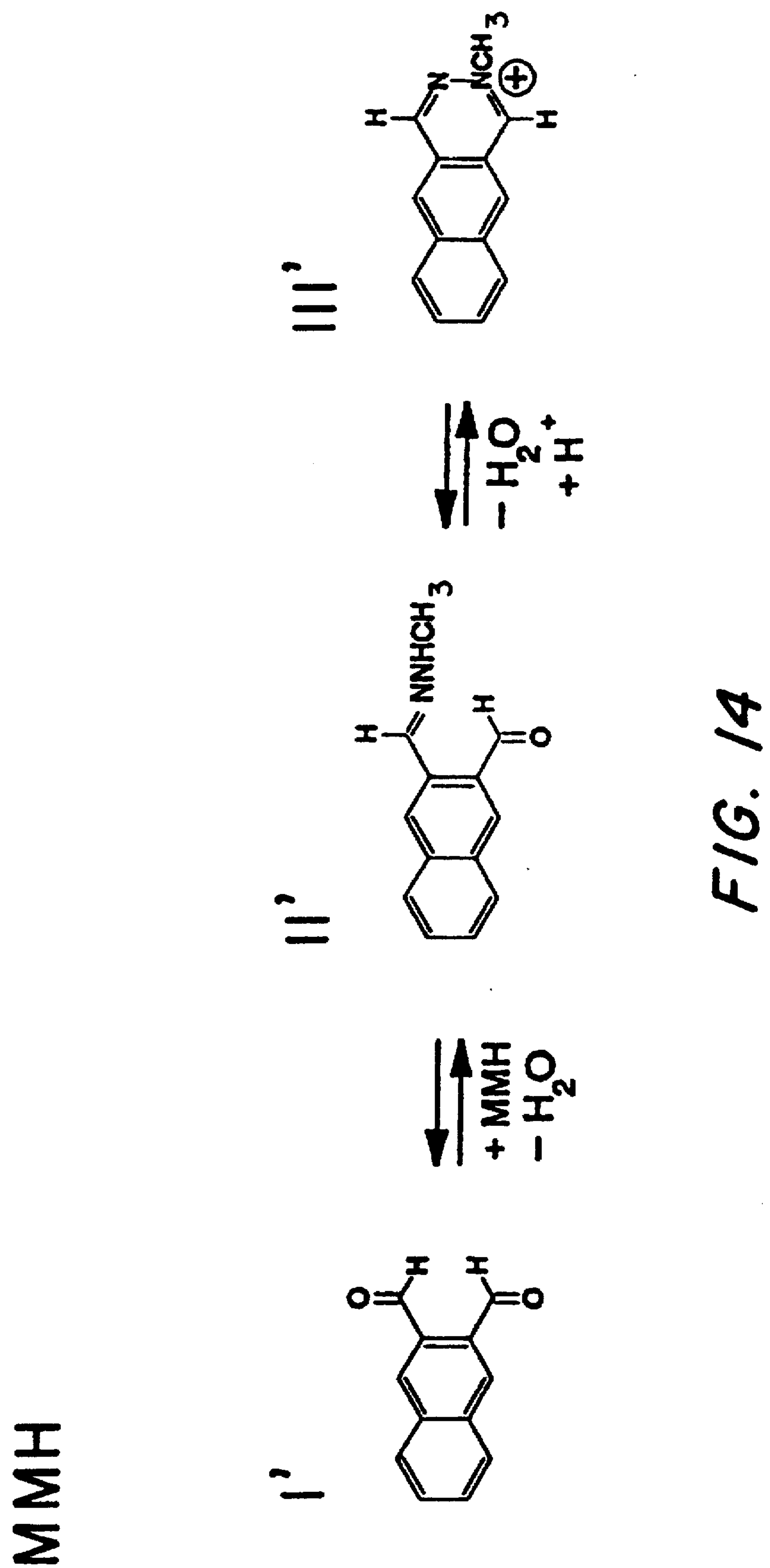

FIG. 14 depicts the reaction mechanism for the derivatization of MMH by NDA.

Figure 15:
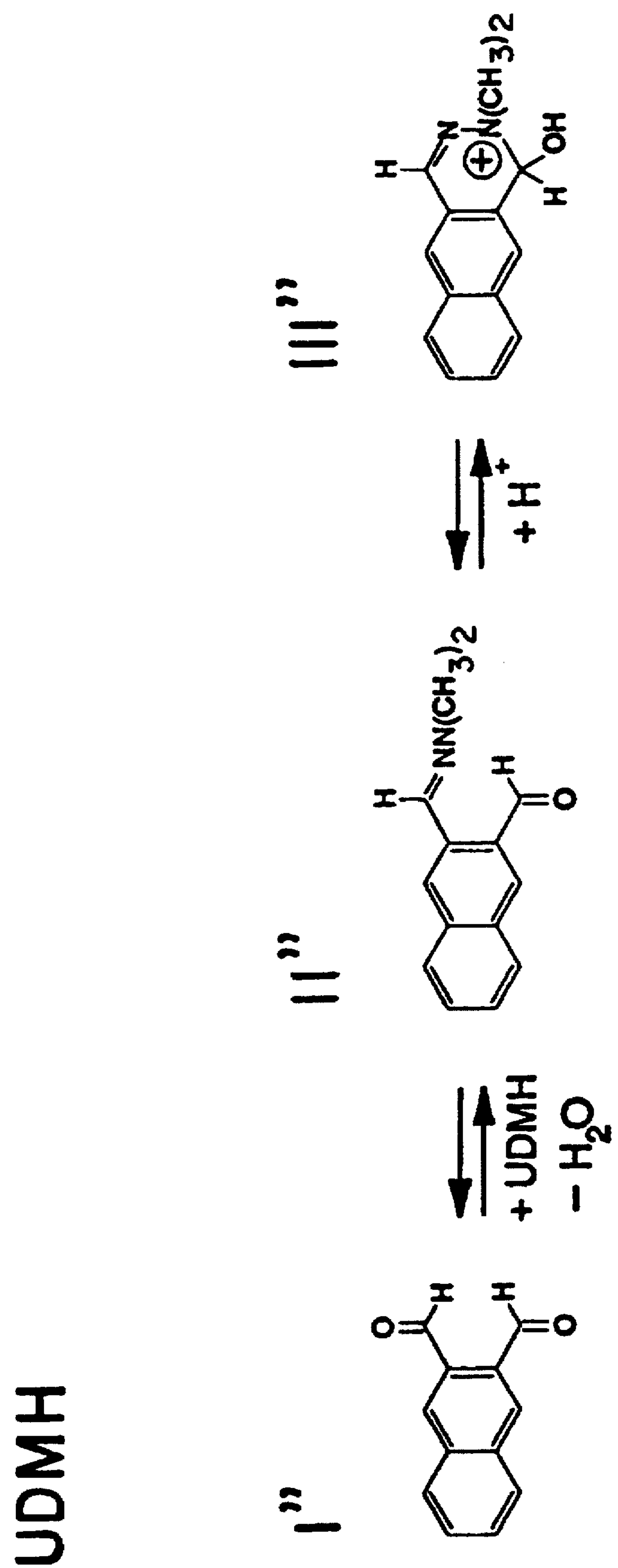

FIG. 15 depicts the reaction mechanism for the derivatization of UDMH by

Figure 16:
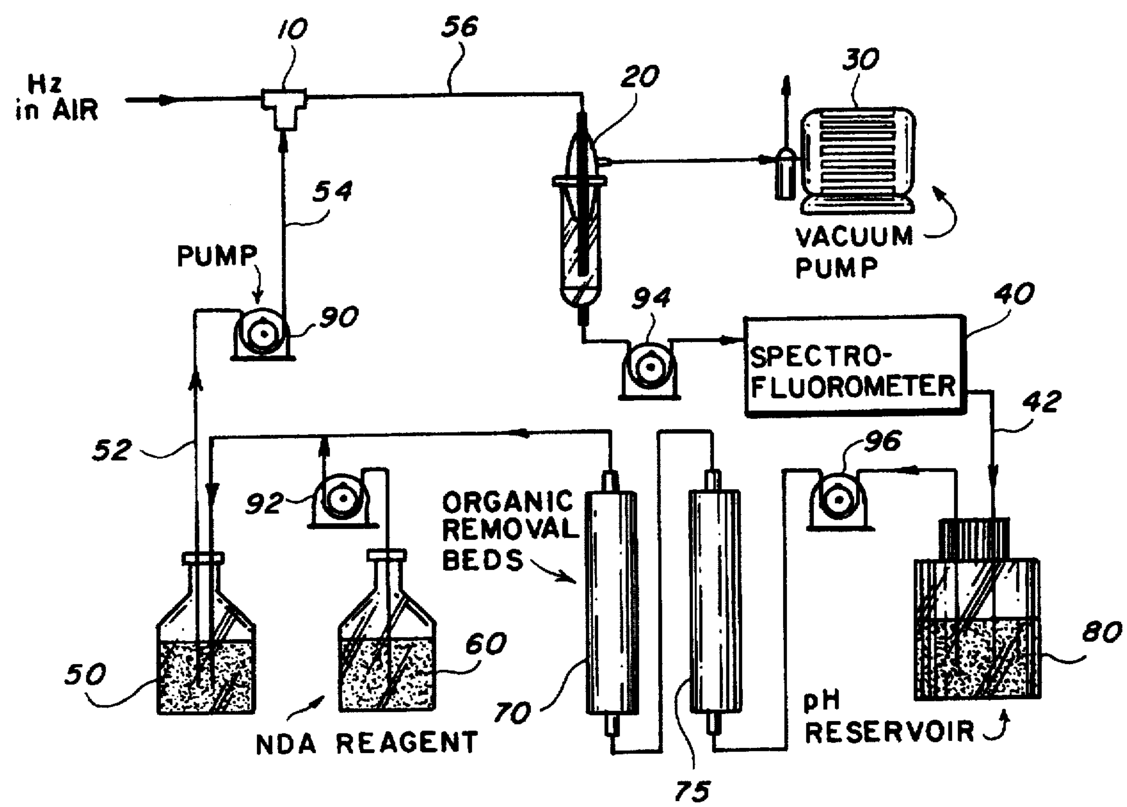

FIG. 16 is a schematic for the continuous flow, fluorimeter system used for trace level hydrazine monitoring in the air. It is a schematic of the hydrazine vapor detection system.

Figure 17:
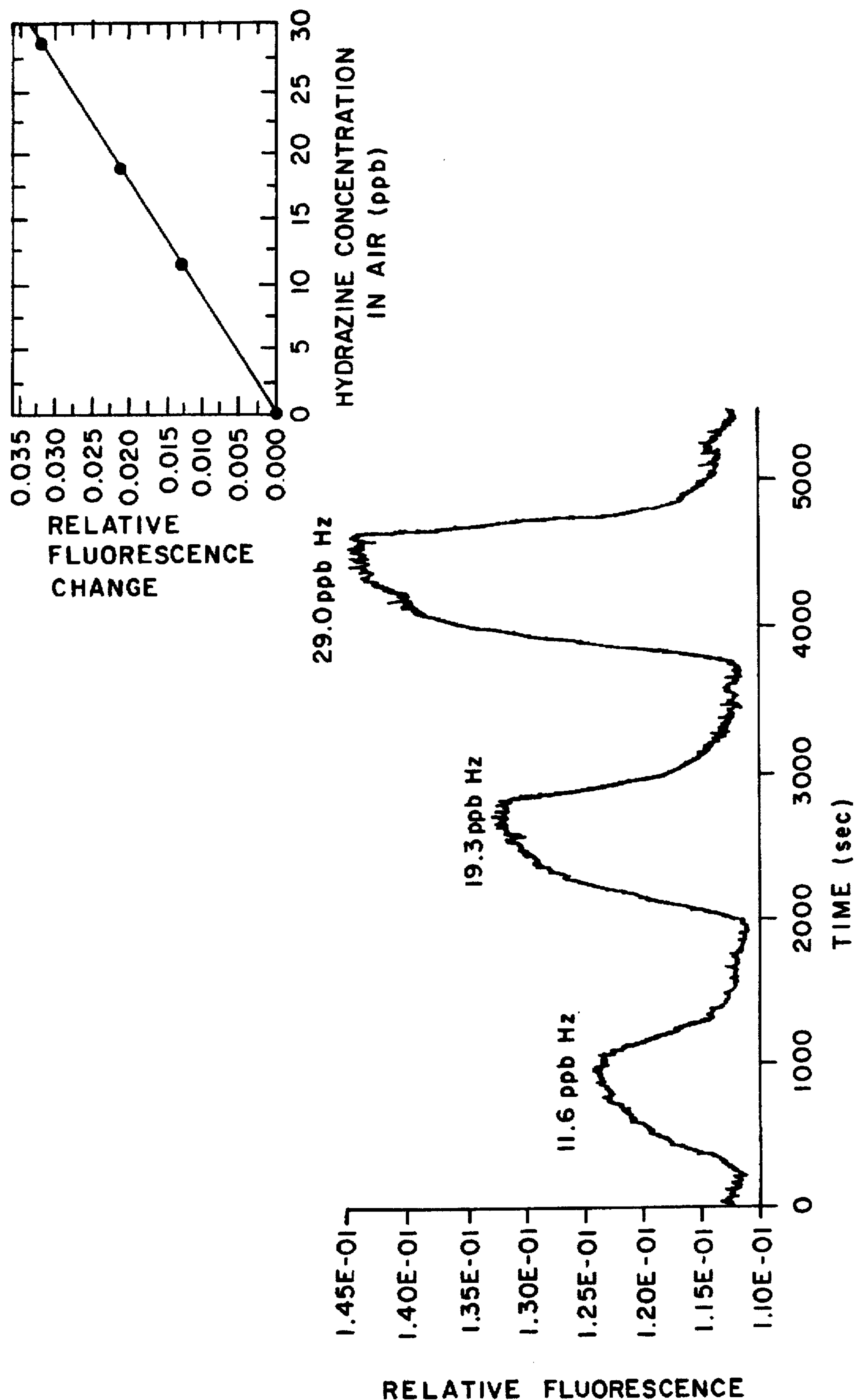

FIG. 17 is a plot of relative fluorescence versus time and an inset plot of relative fluorescence change versus hydrazine concentration in air (ppb). The plot of relative fluorescence versus time is the quantitative response curve to the introduction of three different levels of hydrazine.

DETAILED DESCRIPTION OF THE PREFERRED EMBODIMENTS

The following detailed description of the invention is provided to aid those skilled in the art in practicing the present invention. However, the following detailed description of the invention should not be construed to unduly limit the present invention. Variations and modifications in the embodiments discussed may be made by those of ordinary skill in the art without departing from the scope of the present inventive discovery.

Figure 1:
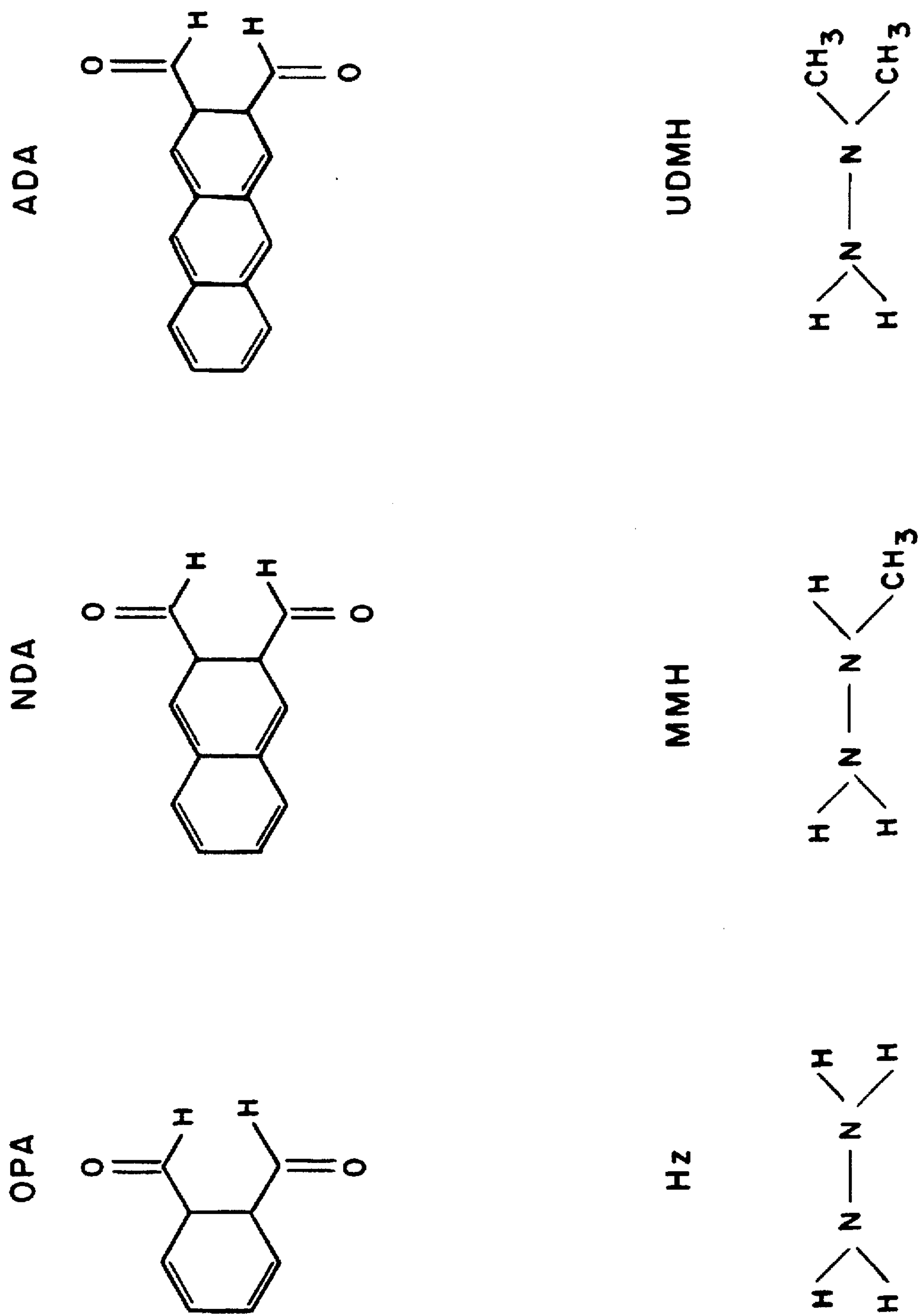

FIG. 1 depicts the molecular structures of the aromatic dicarboxaldehyde derivatizing agents (OPA, NDA and ADA) and the hydrazines (Hz, MMH and UDMH) to be detected by the method of the presently disclosed invention. FIG. 10 indicates the excitation wavelengths ($\lambda_{ex}$) and the center of the emission wavelength range ($\lambda_{em}$) used for the detection of the different hydrazine derivatives formed by the reaction between the aromatic dicarboxaldehyde derivatizing agents (OPA, NDA and ADA) and the hydrazines (Hz, MMH and UDMH). FIG. 11 outlines the concentrations of the derivatizing agents and the analytes (i.e. the hydrazines—Hz, MMH and UDMH) used for obtaining the pH profiles depicted in FIGS. 4 and 8.

It is important to bear in mind that while the present invention is centered upon methods for the sensitive determination of hydrazine levels present within a working environment (e.g. ppb in air or other gas medium), a flow-through fluorometric technique actually monitors the concentration of hydrazine present in solution (e.g. μg/l of solution). Imperative to the present liquid-based fluorescence scheme for the detection of hydrazine, then, is the capability of efficiently scrubbing trace amounts of hydrazine vapor from the ambient air or other gas medium into an aqueous medium. Studies indicate that a gas-liquid scrubber using acidic water or an aqueous solution of an aromatic dicarboxaldehydes (e.g. including OPA, NDA and/or ADA) will give nearly complete recovery of the hydrazine from the vapor phase into the liquid phase.

A chemical derivatization scheme has been developed for the sensitive and selective determination of hydrazine, monomethylhydrazine (MMH) and 1,1-dimethylhydrazine (UDMH) by fluorescence spectrometry. Incorporation of hydrazine into an aromatic framework by derivatization with ortho-phthalaldehyde (OPA), 2,3-napthalene dicarboxaldehyde (NDA), or 2,3-anthracene dicaroboxaldehyde (ADA), creates an efficient fluorophore whose $\lambda_{em}$ is red-shifted from the original reagent. The fluorescence emission for each of the different derivatizing reagents (OPA, NDA and ADA) is minimal and nearly within the noise of the background. The hydrazine derivatives, on the other hand, are intensely fluorescent and characterized by a broad fluorescence emission centered at 376 nm for OPA, 500 nm for NDA, and 549 nm for ADA, respectively.

Shown in FIG. 13 is a derivatization scheme for the reaction of hydrazine, $N_2H_4$, with 2,3-naphthalene dicarboxaldehyde (NDA). The initial reaction between Hz and NDA involves the nucleophilic attack of one of the lone pair of electrons on the Hz toward an aldehyde group on the NDA. The alcoholic intermediate, II, formed is believed to be unstable, quickly losing a molecule of water to form the hydrazone shown as molecule, III. The proximity of the remaining lone pair of electrons on the hydrazone to the remaining aldehyde group, enables a similar set of reaction steps to complete the cyclization of the NDA reagent to form 2,3-diazaanthracene, V.

There are likely two different acid-catalyzed pathways evident in FIG. 13: 1) protonation of an aldehyde group in either molecule I or III, creating a new functional group which is more susceptible to attack by the nucleophilic hydrazine (I→II and III→IV); and, 2) protonation of the hydroxyl group in either intermediate II or IV to form the weakly basic and significantly improved leaving group, $—OH_2^+$ (II→III and IV→V). GC/MS has corroborated the formation of the hydrazone, III ($C_{12}H_{10}ON_2$; m/z=198 (25%), 186 (12%), 154 (36%), 126 (100%)), as well as the final condensation product, V ($C_{12}H_8N_2$; m/z=180 (100%), 153 (20%), 126 (70%)). In addition, OPA and ADA have been observed to react with hydrazine in an analogous fashion to the derivatization scheme shown in FIG. 13 for NDA; CID mass spectrometry has verified the formation of phthalazine ($C_8H_6N_2$; m/z=130) and 2,3-diazanaphthalene ($C_{16}H_{10}N_2$; m/z=230) in the two respective reactions.

FIG. 14 depicts a reaction mechanism for the formation of the fluorescent derivative III' formed by the reaction of MMH and NDA. FIG. 15 depicts a reaction mechanism for the formation of the fluorescent derivative III" formed by the reaction of UDMH and NDA.

Figure 2:
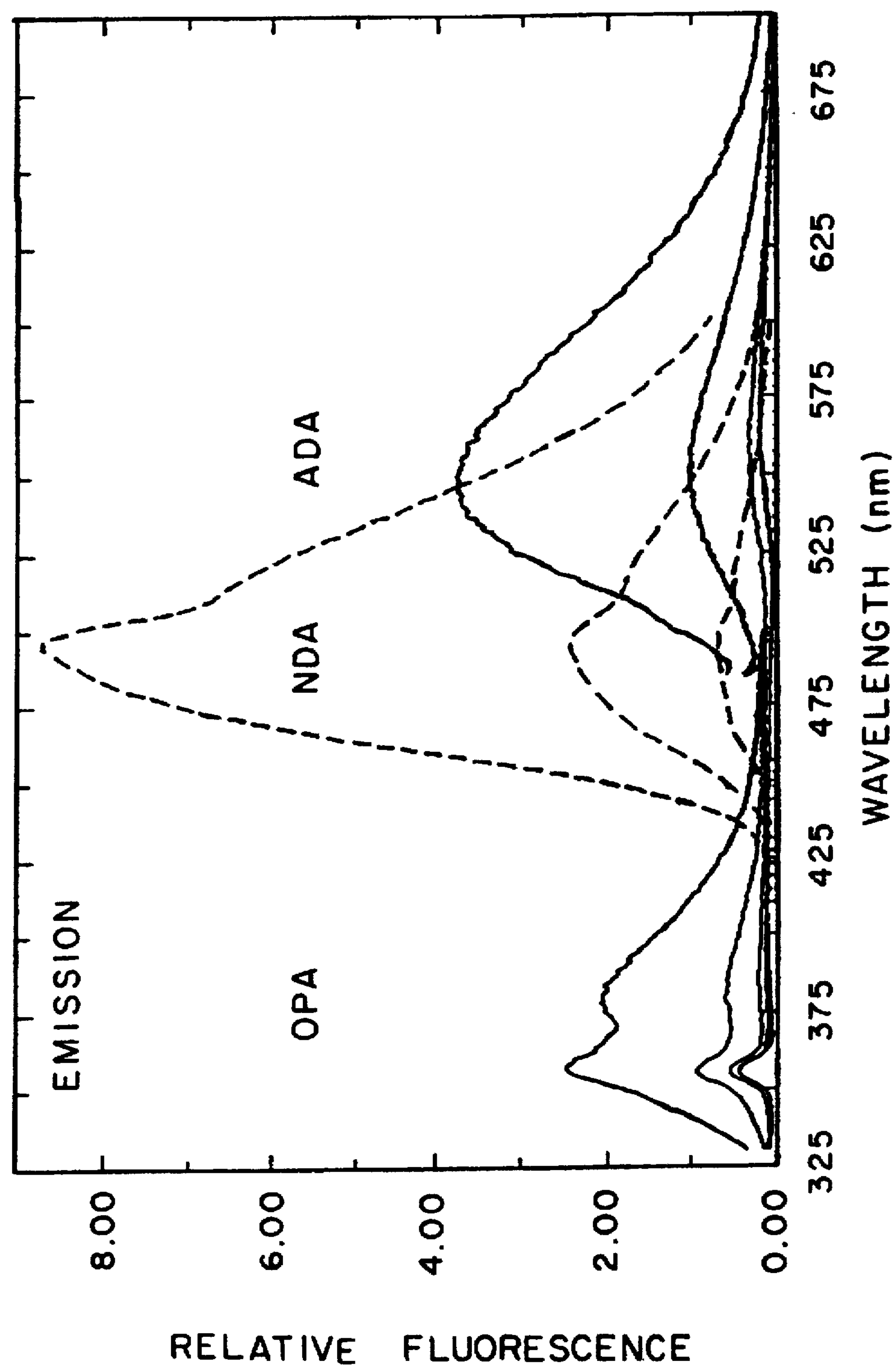
Figure 3:
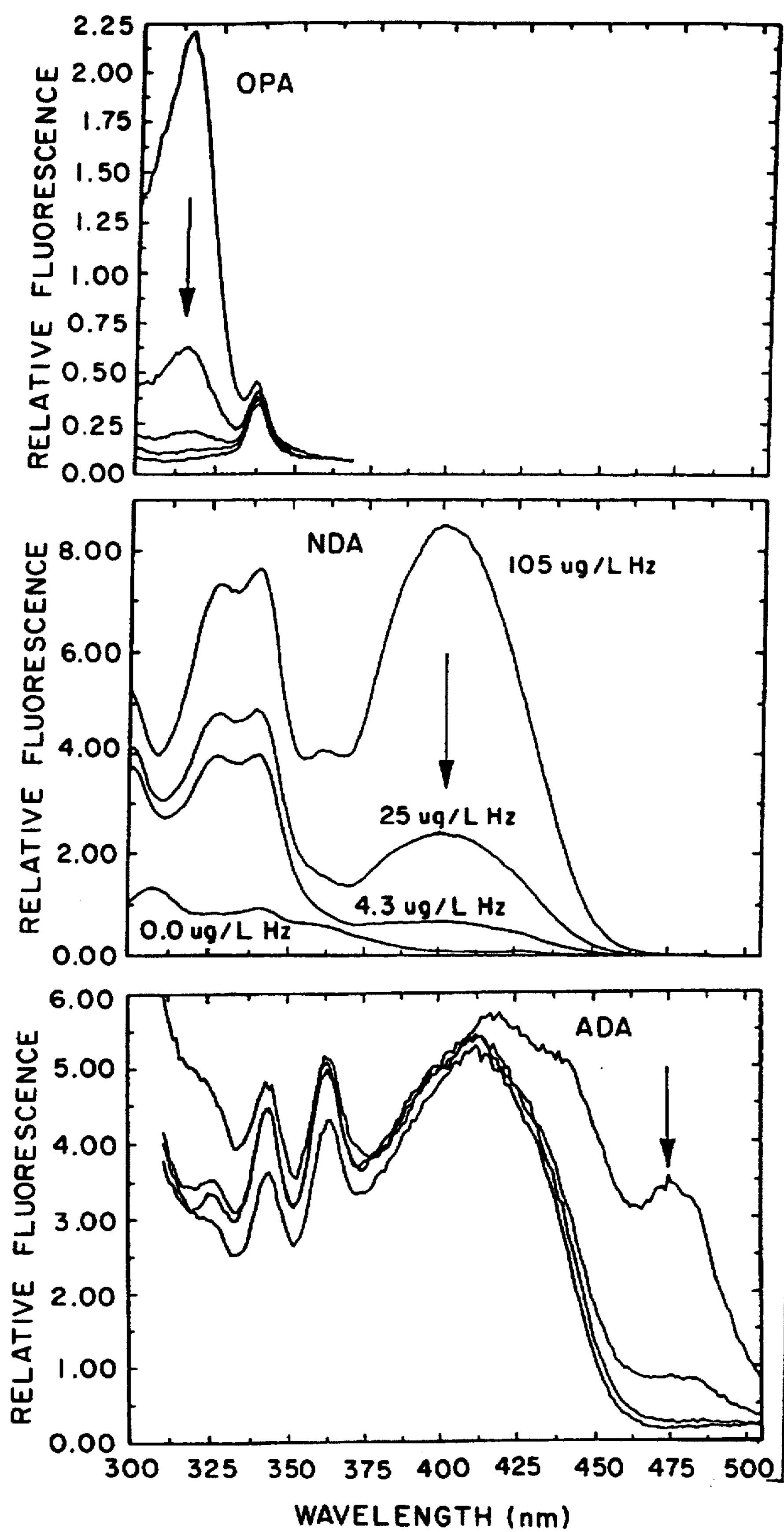
FIG. 3 is the excitation spectra obtained for OPA, NDA, and ADA following the addition of 0, 4.3, 25, and 105 μg/L of hydrazine to the OPA, NDA and ADA reagent solutions, respectively. In addition, the excitation spectrum from the addition of 440 μg/L of hydrazine to the OPA reagent is shown.

The incorporation of hydrazine into an aromatic framework, such as benzene, naphthalene or anthracene, as an additional, fused, six-membered heterocycle, results in the formation of a highly efficient fluorophore whose $\lambda_{em}$ is red-shifted away from the fluorescent spectrum of the original compound. FIG. 2 contains a set of emission spectra collected for NDA ($\lambda_{ex}$=403 nm; $\lambda_{em}$=500 nm), for ADA ($\lambda_{ex}$=476 nm; $\lambda_{em}$=549 nm) and for OPA ($\lambda_{ex}$=318 nm; $\lambda_{em}$=376 nm) following the sequential addition of 0, 4.3, 25 and 105 μg/L of hydrazine to the NDA, ADA and OPA reagent solutions, respectively. Note that prior to the addition of any Hz, the fluorescence emission for the reagents NDA, OPA and/or ADA, are minimal and nearly within the noise of the background. The resultant derivative formed by the addition of Hz, on the other hand, is intensely fluorescent and characterized by a broad fluorescence emission centered at 376 nm for OPA, at 500 nm for NDA and at 549 nm for ADA, respectively, and whose fluorescence increases in proportion to the concentration of Hz in solution.

As seen from FIG. 6 and the inset of FIG. 9, for the NDA/Hz derivative, a linear concentration dependence is observed from 50 ng/L to 500,000 ng/L (i.e. 500 μg/L) of hydrazine (correlation coefficient, r>0.999). Following the sequential addition of hydrazine from 100 ng/L to 500 μg/L (see FIG. 9), the fluorescence response seen for NDA/Hz was examined as a function of time. As seen from FIGS. 5, 7, and 9, the response time necessary to give 90% of a full-scale response is <2 minutes. With each subsequent addition of hydrazine (i.e. NDA/Hz; FIG. 2 and FIG. 9), the fluorescence at 500 nm (i.e. for NDA/Hz) increases proportionally. As seen from the inset of FIG. 9, the NDA reagent gives excellent linear response to hydrazine concentration (i.e. between 50 ng/L to 500 μg/L) as well as at significantly higher concentrations.

Similarly, the response of the ADA reagent (i.e. for ADA/Hz) is also linear. However for the ADA/Hz derivative, the response time to give 90% of full-scale response is more rapid (i.e. less than 30 seconds) and its detection limit is higher (200 ng/L).

The selectivity of NDA and ADA with respect to the fluorescent detection of hydrazine, MMH and/or UDMH is an additionally attractive feature of this derivatization scheme. The fluorescence response of the NDA reagent, for example, was examined with respect to several likely interferents, such as, ammonia, Freon 113™, isopropyl alcohol, ethanol and methyl ethyl ketone; in all cases, there was no measurable or detectable response at the $\lambda_{em}$ of 500 nm. Furthermore, by careful control of the aqueous pH, it is possible to quantitatively differentiate between the hydrazine and MMH levels present within a given sample. For example, ADA reacts to form a strongly fluorescent derivative with hydrazine ($\lambda_{em}$=549 nm) while forming a non-fluorescent derivative with both MMH and UDMH. As can be seen in FIGS. 4 and 8 (both figures are plots of the rate constant (k) versus the pH), the analytical detection of the ADA/Hz derivative is optimum at a pH of 11. NDA, on the other hand, forms an intensely fluorescent derivative ($\lambda_{em}$= 500 nm) with Hz (at pH 2.5), with UDMH (at pH 9) and MMH (at pH 9); the derivative formed with UDMH is nearly a 100 times less intense, and, therefore, is not an interferant at the concentration levels of 200 µg/L or less of UDMH.

Reaction order kinetics were examined for each of the different reagents (OPA, NDA, and ADA) in their reaction with Hz, and the results provide further support for the derivatization scheme presented in FIG. 13. In each case, a plot of the observed rate constant, $k_{obs}$, versus the concentration of hydrazine in solution showed excellent linear correlation, suggesting that the reactions are each first order with respect to the hydrazine concentration (R=0.99 for OPA, R=0.99 for NDA and R=0.99 for ADA). Similarly, a linear dependence was observed between $k_{obs}$ and the concentration of NDA and ADA, indicating that both of these reactions are first order in the dicarboxaldehyde concentration (R=0.98 for NDA, and R=0.99 for ADA). In the case of OPA, increasing concentrations of OPA (with [OPA]>>>> [Hz]) resulted in a bell-shaped curve; the decrease seen in the observed rate constant at high concentrations of OPA likely arises from a competing side reaction forming a non-fluorescent derivative at the emission wavelength being probed.

As expected, pH plays an important role in determining the rates of formation for each of the fluorescent derivatives arising from the reaction between hydrazine and the three different dicarboxaldehydes. FIG. 4 is a plot of the observed rate constant as a function of the pH for each of the different aromatic dicarboxaldehydes. Two observations are particularly noteworthy: 1) while NDA and OPA bear reaction maxima at pH 2.5, ADA is optimal at a pH of 11; and, 2) the rate constant, k, for the reaction involving ADA is nearly three orders of magnitude larger than that found for NDA and OPA. Despite the similarity in structure for the reagents within this homologous series, it is evident that the nature of the reaction for the formation of the fluorescent derivative is different for the ADA reagent. Further examinations into the nature of the reaction between hydrazine and NDA have indicated that the NDA/hydrazine derivative is actually a fluorescent, pH indicator which is fluorescent only under acidic conditions (i.e. pH<4). Apparently, it is the conjugate acid of 2,3-diazaanthracene V, or species VI, which is actually the fluorescent molecule detected at a $\lambda_{em}$ of 500 nm. If the pH is subsequently adjusted to a neutral or basic pH, the NDA/hydrazine derivative (molecule V) becomes undetectable at the same excitation and emission wavelengths. We can readily cycle between the fluorescent and non-fluorescent forms of this derivative (V⇆VI) by simply changing the pH of the solution. As we might expect from FIG. 4, the OPA/hydrazine derivative behaves in a similar manner to the NDA/hydrazine derivative, exhibiting its fluorescent behavior only under acidic conditions. In contrast to these observations, though, the ADA/hydrazine derivative is fluorescent at basic pH values (pH>7), or, apparently, when the derivative is in the neutral or conjugate base form. By careful control of the pH and the aromatic dicarboxaldehyde chosen, it is possible to quantitatively differentiate between the hydrazine, MMH, and UDMH levels present in mixed samples.

MMH and UDMH do not form fluorescent products upon reaction with ADA. From an analytical standpoint, the critical factor is that ADA serves as a highly selective reagent for Hz, even in the presence of structurally similar hydrazines. The diversity in reactivity apparent between the three dicarboxaldehydes makes it possible to quantitatively differentiate between the structurally similar hydrazines through careful control of the pH.

The kinetic rate of formation of each of the derivatives is highly pH dependent, as indicated by FIGS. 4 and 8. The nature of these properties make it possible to quantitate the hydrazine, MMH and UDMH levels present within a given sample by making a set of measurements: 1) the concentration of hydrazine in solution can be determined by using the highly selective reagent, ADA, at a pH of 11 and monitoring the fluorescence response at 549 nm; 2) the concentration of (MMH+UDMH) in solution can be evaluated using NDA at a pH of 9 ($\lambda_{em}$=500 nm)–the fluorescent response of the NDA/UDMH derivative is negligible at UDMH concentrations below 200 ug/L; and, 3) the total concentration of (Hz+MMH) in solution can be determined by simply lowering the pH of the solution described in (2), and measuring the fluorescence at $\lambda_{em}$=500 nm.

In order to evaluate the accuracy of this methodology, a mixture of 22.5 ug/L Hz, 22.5 ug/L UDMH and 33.0 ug/L MMH was analyzed for a determination of the Hz and MMH levels. The mixture was first examined at a pH of 11 using ADA, and the fluorescent response, which was selective to the concentration of Hz in solution, gave a value of 23.6±0.8 ug/L of hydrazine in solution. The concentration of MMH in solution was determined by analyzing the fluorescent response following the addition of NDA at a pH of 9. In this case, the UDMH concentration was low enough to prevent any interference. The value obtained for the MMH concentration was 35.2±1.4 ug/L. Finally, the hydrazine concentration was determined once again, by using the NDA reagent to determine the (MMH+Hz) concentration evident at pH 2. In combination with the results obtained at pH 9 using the NDA reagent, the Hz concentration in solution was calculated to be 22.3±1.1 ug/L.

FIGS. 5 and 6 illustrate the dramatic differences in reactivity and sensitivity apparent between the three different dicarboxaldehydes examined. In order to permit an equal comparison, each of the reactions with hydrazine were done using the optimal pH (OPA and NDA–pH 2.5; ADA–pH 11) and fluorimetric parameters for each particular reagent. FIG. 5 is a plot of the change in fluorescence as a function of time for OPA, NDA and ADA, following the addition of 45 ug/L of hydrazine to the solution. In agreement with FIG. 4, the time response necessary for the formation of the fluorescent ADA/hydrazine derivative is substantially shorter than that for the NDA or OPA derivatives. The fluorescent response levels off after only 10 seconds, and then a small decrease in the response is evident. The NDA/hydrazine derivative, on the other hand, while appearing to possess the largest fluorescence quantum efficiency, has a time response that is significantly longer. This result manifests itself in an improved sensitivity of the NDA reagent for the detection of hydrazine. This observation is confirmed in FIG. 6, a plot of the relative change in fluorescence intensity for OPA, NDA, and ADA as a function of the hydrazine concentration in solution. The sensitivity increases in the order OPA<ADA<NDA. Bear in mind when examining the data pertaining to ADA, that there is a lower light intensity from the Xenon arc lamp at the higher excitation wavelength (476 nm), and, also, that the photomultiplier tube (PMT) will have a lower efficiency for the detection of photons at 549 nm.

Having observed that the rate constant for the formation of the fluorescent NDA/Hz derivative VI at pH 2.5 is nearly 1000 times lower than the rate constant for the fluorescent ADA/Hz derivative at pH 11, the reactivity of NDA with Hz under neutral and basic conditions was investigated. An aliquot of Hz was added to a solution of NDA at pH 8 and allowed to react for two minutes. This was immediately followed by the addition of sufficient acid to lower the pH to 2.5. The reaction was monitored using the spectrofluorometer and compared directly to a control sample in which the same Hz aliquot was added to a solution of NDA already at a pH of 2.5. FIG. 7 displays the results obtained in both cases (i.e. Case 1—NDA solution at initial pH 8, addition of Hz followed by addition of acid to pH 2.5; Case 2—NDA solution at initial pH 2.5 followed by addition of Hz). The results depicted in FIG. 7 indicate that acid conditions prior to the formation of 2,3 diazaanthracene V result in a significant suppression of the formation rate for the fluorescent, conjugate acid, VI.

It is of interest to compare and contrast the reactivity of the different aromatic dicarboxaldehydes with the structurally similar hydrazines, e.g., MMH and UDMH. The addition of one or two methyl groups to the basic hydrazine molecule has a dramatic impact upon the reactivity of these propellents with the different reagents, as well as on the fluorescence properties of the final derivative formed.

Shown in FIG. 8 is a plot of the observed rate constant for the reaction of NDA with Hz, MMH, and UDMH, as a function of the pH. Focussing first on the reaction between NDA and MMH, two observations are apparent from this figure: 1) the optimal pH for the formation of the fluorescent derivative has now shifted from a pH of 2.5 for the NDA/Hz derivative, to a pH of 9 for the NDA/MMH derivative; and, 2) the reaction rate for MMH is on the order of the reaction rates seen previously for the reactions between ADA and hydrazine (see FIG. 4), nearly three orders of magnitude larger than the reaction rate measured between NDA and Hz at pH 2.5. The reaction between NDA and UDMH forms a fluorescent derivative optimally at a pH of 9, the same pH observed in the derivatization of MMH by NDA. It should be pointed out, though, that while the reaction rate for UDMH is of the same order of magnitude as MMH, the sensitivity is substantially lower, with a detection limit that is several orders of magnitude above that found for either MMH or Hz.

The reaction mechanism shown in FIG. 13 is proposed to explain the formation of the intensely fluorescent derivative, VI, the conjugate acid of 2,3-diazaanthracene (V), which is the product formed in the reaction between hydrazine and NDA. The reaction is acid catalyzed and readily takes place in the absence of any added nucleophiles (i.e. $CN^-$ or thiol). The incorporation of hydrazine into the napthalene framework as an additional, fused six-membered heterocycle, results in the formation of a highly efficient fluorophore that emits maximally in the green.

The schematic of the vapor hydrazine detection system depicted in FIG. 16 is further explained below using the exemplary NDA aromatic dicarboxaldehyde. The apparatus of FIG. 16 can be similarly used with the other exemplary aromatic dicarboxaldehydes, OPA and ADA. The system is composed of several different components. A peristaltic pump with multi-channel pumping capability is used for the transport of the exemplary NDA liquid reagent (0.8 ml/min) at various points throughout the system (i.e. pumps 90, 92, 94 and 96). An exemplary concentrated stock solution of the exemplary NDA reagent (2 L at $5.4\times10^{-3}$ M) prepared in a (50%/50% by volume) water/ethanol solution is held in tank 60. The exemplary stock solution of NDA from tank 60 is transported to tank 50 via pump 92. The exemplary stock solution is slowly diluted into acidic water held in tank 50 in order to provide for a $1\times10^{4}$ M active solution. The peristaltic pump 90 delivers the exemplary acidic diluted NDA reagent through a short length of teflon tubing 52, 54, and 56 wherein tubing 56 is concurrently transporting vapor from the outside air or other gas medium (i.e. Hz in air or other gas medium) due to the placement of a vacuum pump 30 upstream. It is this gas/liquid interface which enables the derivatization reaction between the exemplary acidic diluted NDA reagent and hydrazine to take place within tubing 56. The liquid flowing in tubing 56 is then collected in a modified, glass bubbler 20 whereupon the NDA/hydrazine derivative is pumped via pump 94 to spectrofluorimeter 40 and then detected. In order to prevent the production of large quantities of waste, the liquid reagent flowing from spectrofluorometer 40 into reservoir 80 via teflon piping 42, is recycled through a set organic removal columns 70 and 75 (charcoal columns) and the liquid reagent is reused again. Initial characterization of these columns 70 and 75 has shown that the exemplary fluorescent NDA/hydrazine derivative VI is quantitatively removed from the liquid stream, while the starting reagent, NDA I, is reduced in concentration by a factor of 50 (i.e. from $1\times10^{-4}$ M to ($1\times10^{-4}$ M/50)=$2.3\times10^{-6}$ M). Because the exemplary starting reagent of NDA I is non-fluorescent at the wavelengths being probed (i.e. $\lambda_{em}$=500 nm), the presence of NDA I should not present a problem. Note that instead of NDA, either of ADA or OPA stock solutions may be used in their appropriate concentrations and pH. In addition, either of Hz, MMH and/or UDMH may be detected by the exemplary apparatus described above for the detection of Hz using NDA.

Shown in FIG. 17 is an example of the quantitative response obtained from the system depicted schematically in FIG. 16 wherein three different concentrations of hydrazine in air were introduced into the system of FIG. 16. In obtaining the information present in FIG. 17, the exemplary active reagent was a $1\times10^{-4}$ M aqueous solution of NDA adjusted to a pH of 2.5 in sulfuric acid. The liquid flow rate was adjusted to 0.8 ml/min, and the air flow pumping rate was brought to 0.7 L/min. For each different concentration of hydrazine, a cycle of fifteen minutes on and fifteen minutes off was followed. The inset in FIG. 17 is a plot of the fluorescence changes seen following the introduction of each different concentration of hydrazine. The response can be seen to be very linear in nature (r>0.999) bearing a detection limit for hydrazine in air (Signal to Noise Ratio=3) of 2 ppb. The time response for this exemplary sensor is approximately fifteen minutes. However, the time response can be varied from about 2 to about 15 minutes, inclusive, by adjusting the liquid flow rate, with the detection limit being similarly adjusted from approximately 1–10 ppb for Hz in air.

The sensitivity of this vapor detection system can be markedly improved by simply increasing the air sampling rate while keeping the liquid reagent flow rate the same. The net result of this action is an increase in the concentration of the exemplary fluorescent NDA/hydrazine derivative formed in solution. The sensitivity increases nearly linearly with the air flow rate. As the air flow rate increases, though, the concentration of unreacted hydrazine in solution increases as the collection efficiency goes down. This will ultimately give rise to abnormally long response times due to residual hydrazine sticking to the sides of the tubing and glassware.

Additionally, the aromatic dicarboxaldehydes (OPA, ADA and/or NDA) can be deposited or immobilized on a solid support for the fluorescent detection of Hz, MMH and/or UDMH in air or solution. For example, possible solid support systems for immobilizing the aromatic dicarboxaldehyde include hydrogels, polymeric membranes, solvatochromic polymers and filter paper. Possible exemplary instrumental applications of this chemistry include the use of an optical waveguide based device, a fiber optic, a paper tape advancing through a fluorescent reader or a dosimeter badge with a fluorescence reader. Exemplary deposition procedures for immobilizing the aromatic dicarboxaldehyde onto a substrate solid material include the following: dipping a substrate material into a solution of aromatic dicarboxaldehyde (or mixtures thereof), spraying a solution of an aromatic dicarboxaldehyde (or mixtures thereof) or adding crosslinking agents to a polymer network to immobilize an aromatic dicarboxaldehyde or mixtures thereof onto an exemplary hydrogel substrate.

EXPERIMENTAL

Apparatus

All static, fluorescence measurements were made on an SLM-8000 double-beam scanning spectrofluorometer, using a Rhodamine B reference cell to correct for instrument response and fluctuations in the lamp intensity (450 W Xenon arc lamp).

The flow-through fluorescence results were obtained using a GTI/Spectrovision FD-300 dual monochromator fluorescence detector. This system employs a 10 W Xe flash lump (operated at 30 Hz) and a 100 μL flow-through cell. The peristaltic pump used in these studies was a Masterflex 7521-50, which is capable of pumping 10 different channels simultaneously. The vacuum pump was an SKC Airchek Sampler, and the organic removal columns were supplied by Barnstead/Thermolyne, D8904. Pharmed tubing was used for the peristaltic pump, while all other tubing was teflon-coated.

Chemicals and Stock Solutions

All chemicals were used as received from the suppliers. 2,3-Naphthalene dicarboxaldehyde (99%) and 2,3-anthracene dicarboxaldehyde (≈100%) were obtained from Molecular Probes, Inc., and o-phthalaldehyde (97%) was purchased from Aldrich. Stock solutions of NDA and OPA were prepared at a concentration of $10^{-2}$ M in anhydrous ethanol, while solubility limitations for ADA required that an $8\times10^{-4}$ M stock solution be prepared for this reagent. The hydrazine, monomethylhydrazine, and 1,1-dimethylhydrazine standard solutions (Olin Chemicals) were prepared on a daily basis, by diluting the anhydrous hydrazines in purified water (Millipore) to give the following concentrations: 1 μg/L, 10 μg/L, 100 μg/L, 1 mg/L, 10 mg/L, 100 mg/L, and 1000 mg/L. The hydrazine vapor levels were generated by flowing nitrogen across a small, temperature-controlled ampule containing hydrazine, and diluting to the appropriate concentration with air. Vapor level concentrations were verified by coulometry, the details of which are given by J. R. Wyatt et al., in *Coulometric Method for the Quantification of Low-Level Concentrations of Hydrazine and Monomethylhydrazine*, AM. IND. HYG. ASSOC. J. 54(6):285–292 (1993), incorporated herein by reference in its entirety for all purposes. All pH studies were accomplished using 0.1M buffer solutions of either boric acid (pH 6–11) or sodium dihydrogen phosphate (pH 3–5), wherein each buffer solution was adjusted to the appropriate pH with either NaOH or HCl. Those solutions with a pH above 11 were made using NaOH, while those with a pH below 3 were prepared using either $HNO_3$ or $H_2SO_4$ acid.

Procedure

For those experiments employing the SLM-8000 spectrofluorometer, 2 ml of the appropriate buffer solution were pipetted into a quartz cuvette, along with 10–100 μL (Eppendorf microburette) of either the OPA, NDA or ADA stock solutions. The final concentration of reagent in the cuvette was normally 0.02 mM in ADA, or 0.5 mM in either NDA or OPA. All examinations were done at room temperature. Subsequent spiking of these solutions with varying levels of the different hydrazines was accomplished by adding 10–100 μL of solution from the appropriate dilution standard, quickly mixing the solution, and returning the solution to the sample cell for measurements within the spectrofluorometer. The final concentration of the hydrazines in solution ranged from 50 ng/L to 50 mg/L. Unless mentioned otherwise, the fluorescence measurements were made at the pH best suited for the particular reagent being used and the hydrazine being detected, i.e. pH 2.5 for the detection of Hz with NDA or OPA; pH 9 for the detection of MMH with NDA; pH 11 for the detection of Hz with ADA. The following excitation and emission wavelengths were used for the detection of the fluorescent derivatives formed: OPA ($\lambda_{ex}$=318 nm, $\lambda_{em}$=376 nm); NDA ($\lambda_{ex}$=403 nm, $\lambda_{em}$=500 nm); ADA ($\lambda_{ex}$=476 nm, $\lambda_{em}$=549 nm).

For those experiments using the FD-300 fluorimeter, a $1\times10^{-4}$ M NDA solution was employed, and the peristaltic pump was set to deliver 0.8 ml/min.

Kinetic Investigations

Kinetic studies into the nature of the reaction between the hydrazines (Hz, MMH or UDMH) and the different dicarboxaldehyde reagents were conducted by monitoring the rate of fluorescent product formation using the SLM-8000 spectrofluorometer. The kinetic, pH profiles for the derivatization reactions between the aromatic dicarboxaldehydes, OPA, NDA and ADA, and the hydrazines, were acquired using reagent concentrations comparable to those seen in actual analytical applications, i.e. [Hz]<<<[OPA], [NDA], or [ADA]. The reaction dependence of hydrazine was obtained from a plot of the observed rate constant versus the hydrazine concentration in solution, under conditions such that [Hz]>>>[NDA], or [ADA], or [OPA]. Finally, the kinetic order for each of the different dicarboxaldehydes was obtained by plotting the observed rate constant versus the concentration of the reagent in solution, wherein [NDA], or [OPA], or [ADA]>>>[Hz].

Mass Spectrometry

Mass spectrometric results were obtained using either a Varian ITS40 Gas Chromatograph/Quadrupole Ion Trap, or a Finnigan TSQ70 Quadrupole Mass Spectrometer employing $NH_3$ collisional ionization (CI) or fast atom bombardment (FAB).

Additional details are given in G. E. Collins and S. L. Rose-Pehrsson, *Sensitive, fluorescent detection of hydrazine via derivatization with 2,3-napthalene dicarboxaldehyde,* ANALYTICA CHIMICA ACTA, VOL. 284, PP. 207–215 (December 1993); G. E. Collins et al., *The Fluorescent Detection of Hydrazine, Monomethylhydrazine, and 1,1-Dimethylhydrazine by Derivatization with Aromatic Dicarboxaldehydes,* OPTICAL SENSING FOR ENVIRONMENTAL MONITORING, PP. 732–739 (1994); S. L. Rose-Pehrsson, *Current State-of-the-Art in Hydrazine Sensing,* PROCEEDINGS (SENSORS EXPO™) PP. 37–41 (1994); G. E. Collins et al., *The Detection of PPB Levels of Hydrazine Using Fluorescence and Chemiluminescence Techniques,* PROCEEDINGS (SENSORS EXPO™) PP. 1–10 (1994); Collins et al., *Fluorescent Detection of Hydrazine, Monomethylhydrazine, and 1,1-Dimethylhydrazine by Derivatization With Aromatic Dicarboxaldehydes,* ANALYST, VOL. 119, PP. 1907–1913, (August 1994); and Collins et al., *Fluorescent Detection of Hydrazine, Monomethylhydrazine, and 1,1-Dimethylhydrazine by Derivatization With Aromatic Dicarboxaldehydes,* CPIA PUBLICATION 600, PP. 11–20, (1993), and each reference incorporated herein by reference in its entirety and for all purposes.

What is claimed is:

1. A method for the detection of a target species selected from the group consisting of hydrazine, monomethylhydrazine and 1,1-dimethylhydrazine, in a gas or a liquid suspected of containing said target species and having a given target species concentration, said method comprising the steps of:

(a) introducing at time $t_0$ a stream of a gas or liquid suspected of containing said target species into a reagent solution having a buffer controlled pH, said reagent solution containing reagent consisting essentially of said buffer and one or more aromatic ortho dicarboxaldehydes to react with said target species to produce a reacted reagent solution including a reacted target species;

(b) exposing said reacted reagent solution to an excitation wavelength range at time $t_1$; and (c) determining the presence of said reacted target species in said reacted reagent solution by monitoring an emission from said exposed reagent solution at an emission wavelength range at time $t_2$.

2. The method of claim 1 wherein said gas stream suspected of containing said target species is introduced into said reagent solution at a rate of at least about 0.100 L/min.

3. The method of claim 1 wherein said gas stream suspected of containing said target species is introduced into said reagent solution at a rate between about 0.100 L/min to about 2.00 L/min, inclusive.

4. The method of claim 1 wherein said aromatic dicarboxaldehyde is selected from the group consisting of orthophthaldehyde (OPA), 2,3-napthalene dicarboxaldehyde (NDA), 2,3-anthracene dicarboxaldehyde (ADA) or mixtures thereof.

5. The method of claim 4 wherein said reagent solution has a concentration of said OPA of about $10^{-8}$ to about $10^{-2}$ moles per liter in water and a pH of about 4.0 or less wherein said target species is said hydrazine and said excitation wavelength range is 318 nm±50nm and said emission wavelength is centered at 376 nm and has a range of 376 nm±75 nm.

6. The method of claim 5 wherein said pH is between about 1.5–3.

7. The method of claim 6 wherein said emission wavelength range is centered at 376 nm±10 nm.

8. The method of claim 4 wherein said reagent solution has a concentration of said OPA of about $10^{-8}$ to about $10^{-2}$ moles per liter in water and a pH of about 7.0 or greater, said target species is said monomethylhydrazine or said 1,1-dimethylhydrazine, said excitation wavelength range is 318 nm±50 nm, and said emission wavelength is centered at 376 nm.

9. The method of claim 8 wherein said pH is about 9.0.

10. The method of claim 9 wherein said emission wavelength range is centered at 376 nm±10 nm.

11. The method of claim 4 wherein said reagent solution has a concentration of said NDA of about $10^{-8}$ to about $10^{-2}$ moles per liter in water and a pH of about 4.0 or less wherein said target species is said hydrazine and said excitation wavelength range is 403 nm±75 nm and said emission wavelength is centered at 500 nm and has a range of 500 nm±100 nm.

12. The method of claim 11 wherein said pH is no greater than about 3.

13. The method of claim 12 wherein said emission wavelength range is centered at 500 nm±10 nm.

14. The method of claim 4 wherein said reagent solution has a concentration of NDA of about $10^{-8}$ to about $10^{-2}$ moles per liter in water and a pH of about 7.0 or greater, wherein said target species is said monomethylhydrazine or said 1,1-dimethylhydrazine, said excitation wavelength range is 403 nm±75 nm, and said emission wavelength range is centered at 500 nm.

15. The method of claim 14 wherein said pH is between about 8–10.

16. The method of claim 15 wherein said emission wavelength range is centered at 500 nm±10 nm.

17. The method of claim 4 wherein said reagent solution has a concentration of said ADA of about $10^{-8}$ to about $10^{-2}$ moles per liter in water and a pH of about 7.0 or greater wherein said target species is said hydrazine and said excitation wavelength range is 476 nm±50 nm and said emission wavelength is centered at 549 nm and has a range of 549 nm±100 nm.

18. The method of claim 17 wherein said pH is about 8–12.

19. The method of claim 18 wherein said emission wavelength range is centered at 549 nm±10 nm.

20. The method of claim 1 wherein said time $t_2$ minus said time $t_0$ is about 2 to about 15 minutes and said concentration of said hydrazine or said monomethylhydrazine in said stream is about 1 ppb to about 10 ppb.

21. The method of claim 20 wherein said time is about 2 to about 10 minutes.

22. The method of claim 20 wherein said time is about 2 to about 10 minutes and said concentration of said monomethylhydrazine in said gas is about 4 parts per billion or greater.

23. The method of claim 1 wherein said time $t_2$ minus said time $t_0$ is about 2 to about 15 minutes and said concentration of said 1,1-dimethylhydrazine in said stream is about 4 to about 6 parts per million.

24. The method of claim 23 wherein said time is about 2 to about 10 minutes.

25. The method of claim 1 wherein said time $t_2$ minus said time $t_0$ is about 2 to about 10 minutes and said concentration of said hydrazine in said liquid is about 50 ng/L or greater.

26. The method of claim 1 wherein said time $t_2$ minus said time $t_0$ is about 2 to about 10 minutes and said concentration of said monomethylhydrazine in said liquid is about 200 ng/L or greater.

27. The method of claim 1 wherein said time $t_2$ minus said time $t_0$ is about 2 to about 10 minutes and said concentration of said 1,1-dimethylhydrazine in said liquid is about 200 μg/L or greater.

28. A method for the detection and quantitation of a target species being one or more of hydrazine, monomethylhydrazine and 1,1-dimethylhydrazine, said method comprising the steps of:

(a) introducing a stream of a gas or liquid suspected of containing said target species into
   (i) an anthracene ortho-dicarboxaldehyde (ADA) reagent solution having a pH of from about 7 to 14 to form an ADA sample solution;
   (ii) a naphthalene ortho-dicarboxaldehyde (NDA) reagent solution having a pH of from about 7 to 11 to form a first NDA sample solution; and
   (iii) a naphthalene ortho-dicarboxaldehyde (NDA) reagent solution having a pH of less than about 3 to form a second NDA sample solution;

(b) exciting each of said sample solutions at an excitation wavelength corresponding to a fluorescent excitation wavelength of a reaction product of said corresponding reagent and said target species;

(c) recording emissions from each of said sample solutions at an emission wavelength corresponding to said fluorescent emission wavelength of said reaction product of said corresponding reagent and said target species, and (d) calculating, from said recorded emissions, concentrations of said target species.

29. The method of claim 28 wherein (i) said ADA sample solution excitation wavelength has a range between about 426 nm to 526 nm;

(ii) said first NDA sample solution has a range between about 328 nm to 478 nm;

(iii) said second NDA sample solution excitation wavelength has a range between about 328 nm to 478 nm;

(iv) said emission of said ADA sample solution is recorded at a wavelength between about 449 nm to 649 nm;

(v) said emission of said first NDA sample solution is recorded at a wavelength of from about 400 nm to 600 nm, and (vi) said emission of said second NDA sample solution is recorded at a wavelength of between about 400 nm to 600 nm.

30. A method for the detection and quantitation of a target species selected from the group consisting of hydrazine, monomethylhydrazine, 1,1-dimethylhydrazine and mixtures thereof, in a gas or a liquid suspected of containing said target species having a given target species concentration, the method comprising the steps of:

(a) introducing at time $t_0$ a stream of a gas or liquid suspected of containing said target species into a reagent solution having a buffer controlled pH, said reagent solution containing a reagent consisting essentially of said buffer, and a members selected from the group consisting of anthracene ortho-dicarboxaldehyde, naphthalene ortho-dicarboxaldehyde, and mixtures thereof to react with said target species;

(b) exposing said reacted reagent solution to an excitation wavelength range at time $t_1$, and (c) monitoring an emission from said exposed reagent solution at an emission wavelength range at time $t_2$ (d) determining, from said monitored emissions, concentrations of said target species.

31. A method for the detection of a target species selected from the group consisting of hydrazine, monomethylhydrazine, 1,1-dimethylhydrazine, and mixtures thereof, in a gas or a liquid suspected of containing said target species having a given target species concentration, said method comprising the steps of:

(a) introducing at time $t_0$ a stream of a gas or liquid suspected of containing said target species into a first and a second reagent solution, each having a buffer controlled pH, wherein said first reagent solution contains a reagent consisting of said buffer and anthracene ortho-dicarboxaldehyde and said second solution contains a reagent consisting of said buffer and naphthalene ortho-dicarboxaldehyde to react with said target species;

(b) exposing said reacted reagent solution to an excitation wavelength range at time $t_1$, and (c) determining the presence of said reacted target species in said reacted reagent solution by monitoring an emission from said exposed reagent solution at an emission wavelength range at time $t_2$.

* * * * *